(12) United States Patent
Brown

(10) Patent No.: US 11,304,830 B2
(45) Date of Patent: Apr. 19, 2022

(54) FLEXIBLE MULTI USE POST OPERATIVE PROSTHETIC SOCKET SYSTEM

(71) Applicant: Robert Brown, Henderson, NV (US)

(72) Inventor: Robert Brown, Henderson, NV (US)

(*) Notice: Subject to any disclaimer, the term of this patent is extended or adjusted under 35 U.S.C. 154(b) by 0 days.

(21) Appl. No.: 16/486,301

(22) PCT Filed: Oct. 10, 2018

(86) PCT No.: PCT/US2018/055155
§ 371 (c)(1),
(2) Date: Aug. 15, 2019

(87) PCT Pub. No.: WO2019/075018
PCT Pub. Date: Apr. 18, 2019

(65) Prior Publication Data
US 2020/0121480 A1    Apr. 23, 2020

Related U.S. Application Data

(60) Provisional application No. 62/696,043, filed on Jul. 10, 2018, provisional application No. 62/667,817, (Continued)

(51) Int. Cl.
*A61F 2/80* (2006.01)
*A61F 2/78* (2006.01)
(Continued)

(52) U.S. Cl.
CPC .............. *A61F 2/80* (2013.01); *A61F 2/7812* (2013.01); *A61F 2002/5007* (2013.01);
(Continued)

(58) Field of Classification Search
CPC .. A61F 2/80; A61F 2/7812; A61F 2002/5007; A61F 2002/5026;
(Continued)

(56) References Cited

U.S. PATENT DOCUMENTS 5,529,575 A * 6/1996 Klotz ........................ A61F 2/80
623/33
5,571,209 A * 11/1996 Brown, Sr. ............... A61F 2/80
623/33
(Continued)

OTHER PUBLICATIONS

Soderberg, Prosthetics and Orthotics International, 2002, 26, 159-162.*

*Primary Examiner* — Jerrah Edwards
*Assistant Examiner* — Mihret Tafesse
(74) *Attorney, Agent, or Firm* — Aleksandar Nikolic; Luis Ormaechea

(57) ABSTRACT

A prosthetic apparatus and system for a trans-tibial amputee consisting of a post-operative interface socket that can be adjusted to accommodate the size of an amputated limb and changes in size of the limb. The prosthetic apparatus includes a lower socket into which the post-operative socket can be inserted, the lower socket being adjustable for changes in size of the post-operative interface socket. The post-operative socket also has a removable upper back shell that immobilizes movement of the knee during an initial recovery phase but can be removed to allow the knee of the amputee to flex.

24 Claims, 20 Drawing Sheets

Related U.S. Application Data filed on May 7, 2018, provisional application No. 62/636,542, filed on Feb. 28, 2018, provisional application No. 62/570,731, filed on Oct. 11, 2017.

(51) Int. Cl.
  *A61F 2/50* (2006.01)
  *A61F 2/60* (2006.01)

(52) U.S. Cl.
  CPC ............... *A61F 2002/5026* (2013.01); *A61F 2002/5027* (2013.01); *A61F 2002/607* (2013.01); *A61F 2002/7862* (2013.01)

(58) Field of Classification Search
  CPC ........ A61F 2002/5027; A61F 2002/607; A61F 2002/7862; A61F 2002/5018; A61F 2002/608; A61F 2002/7881; A61F 2/60
  See application file for complete search history.

(56) References Cited

U.S. PATENT DOCUMENTS

| | | | |
|---|---|---|---|
| 5,728,165 A * | 3/1998 | Brown, Sr. | A61F 2/80 623/33 |
| 10,172,728 B2 * | 1/2019 | Hurley | A61F 2/80 623/33 |
| 2009/0182253 A1 * | 7/2009 | Grim | A61F 5/0585 602/16 |
| 2018/0221178 A1 * | 8/2018 | Steinberg | A61F 2/78 |

* cited by examiner

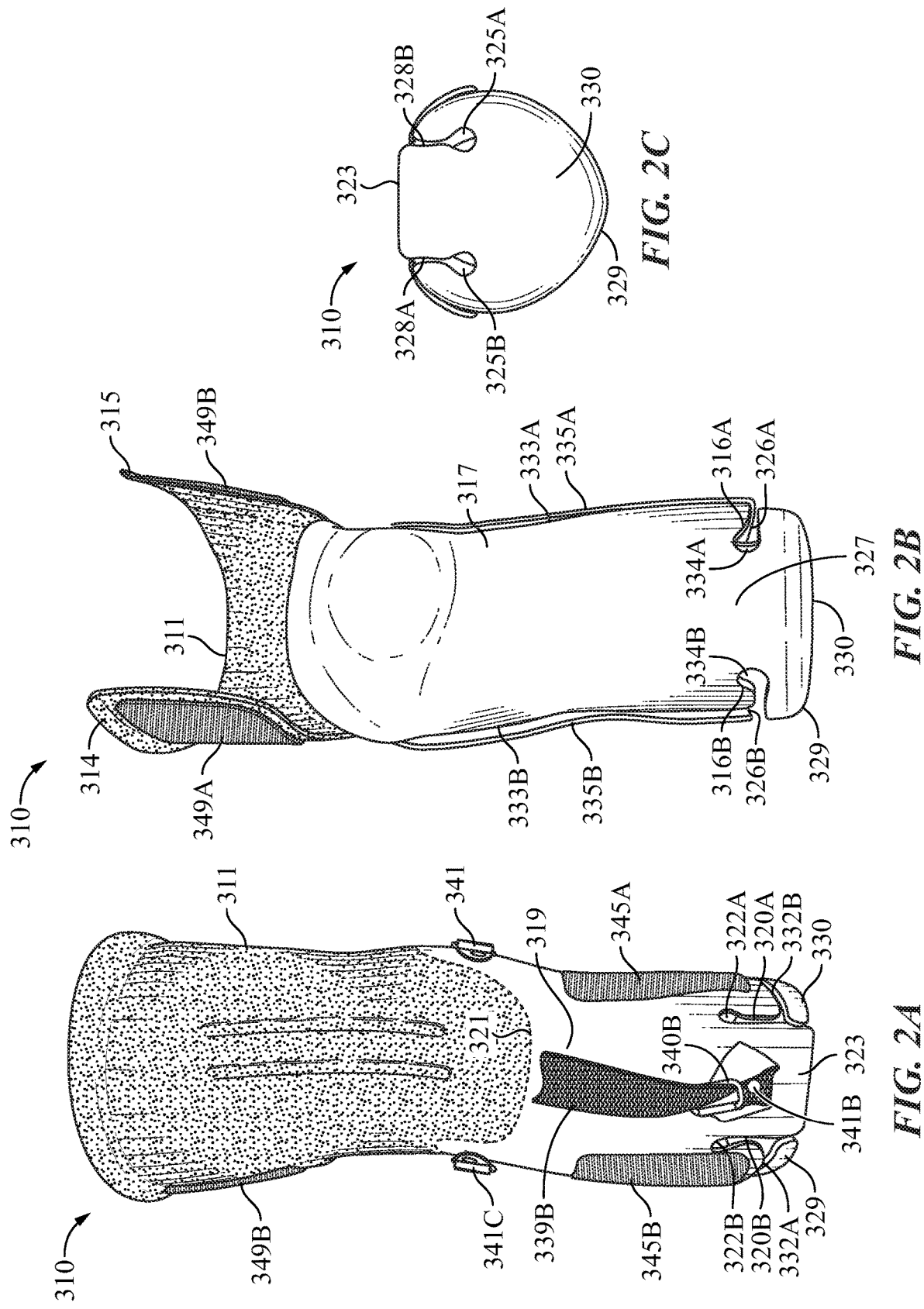

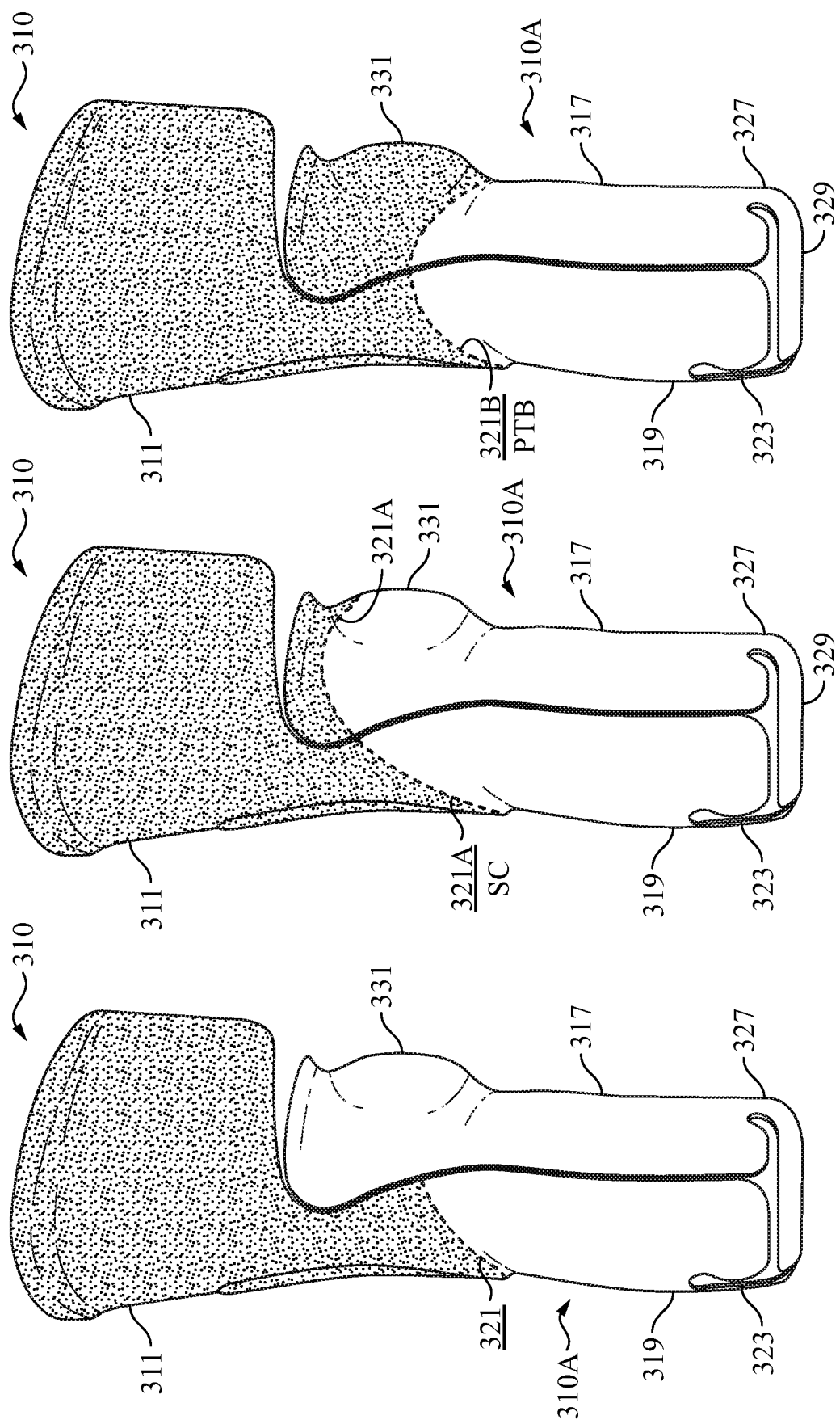

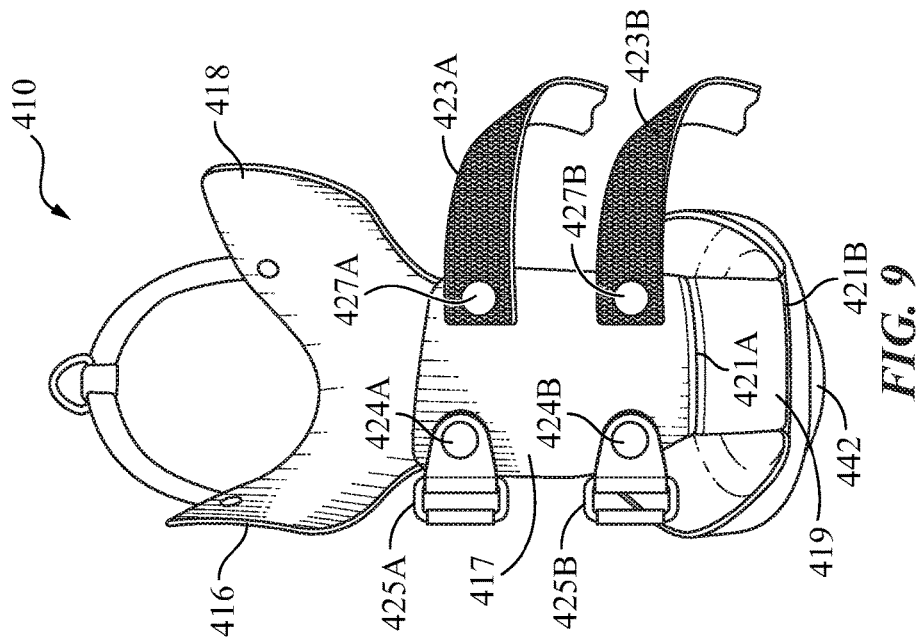
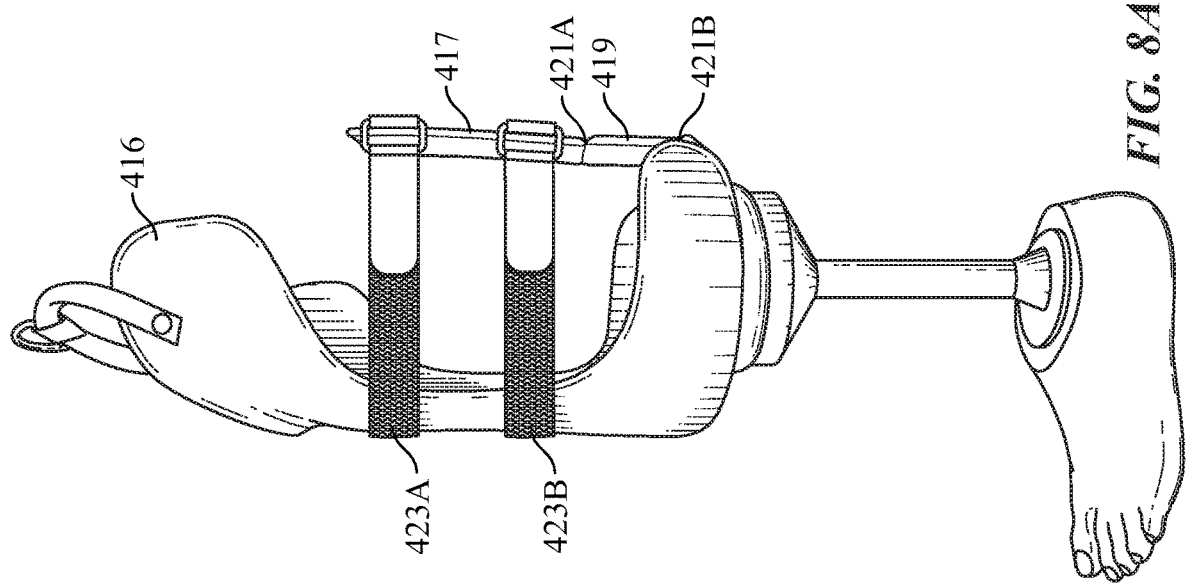

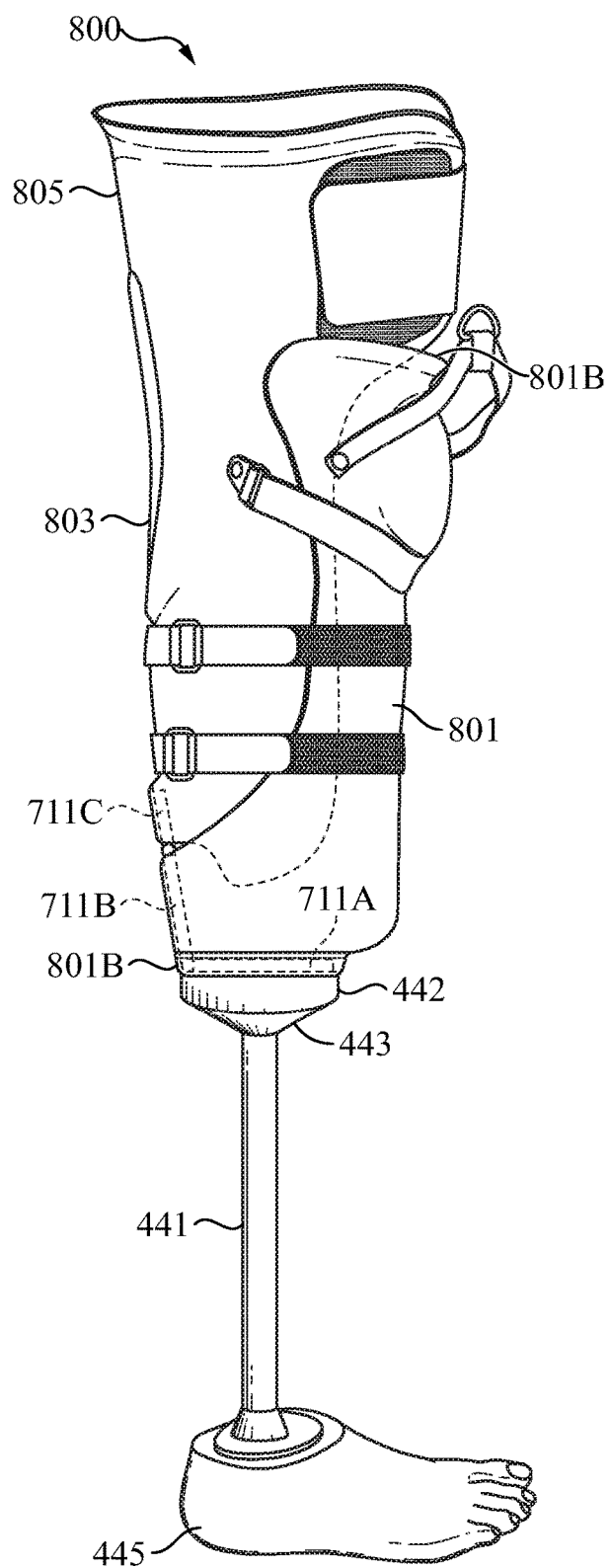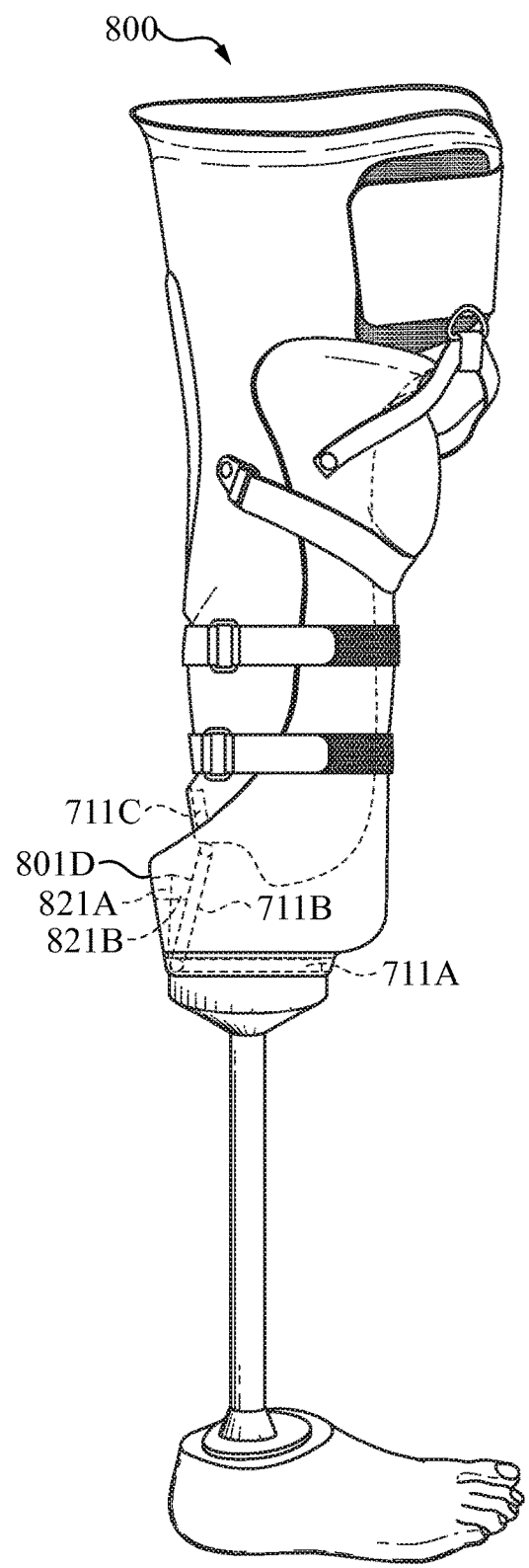
*FIG. 20*      *FIG. 21*

FLEXIBLE MULTI USE POST OPERATIVE PROSTHETIC SOCKET SYSTEM

CROSS-REFERENCE TO RELATED APPLICATIONS

This application claims the benefit of priority under the applicable laws of the United States of: U.S. Provisional Application Ser. No. 62/570,731 filed on Oct. 11, 2017 entitled A FLEXIBLE MULTI USE POST OPERATIVE PROSTHETIC SOCKET SYSTEM, U.S. Provisional Application Ser. No. 62/636,542 filed on Feb. 28, 2018 entitled A FLEXIBLE MULTI USE POST OPERATIVE PROSTHETIC SOCKET SYSTEM, and U.S. Provisional Application Ser. No. 62/667,817 filed on May 7, 2018 entitled A FLEXIBLE MULTI USE POST OPERATIVE PROSTHETIC SOCKET SYSTEM, and U.S. Provisional Application Ser. No. 62/696,043 filed on Jul. 10, 2018 entitled A FLEXIBLE MULTI USE POST OPERATIVE PROSTHETIC SOCKET SYSTEM the contents of all four of which are relied upon and incorporated herein by reference in its entirety.

TECHNICAL FIELD

The disclosure relates generally to a system and apparatus for post-operative prosthetic devices for leg amputees and more particularly for trans-tibial amputees.

BACKGROUND

The present invention is an improvement over the inventions described in U.S. Pat. No. 5,571,209 for a "Post-Operative Protective Prosthesis" (the '209 patent) and U.S. Pat. No. 5,728,165 for an "Adjustable Post-Operative Prosthetic System," (the '165 patent). Both patents—the '209 patent and the '165 patent—are incorporated herein by reference as if set forth herein at length. The '209 discloses a post-operative adjustable protective socket for a patient that has undergone a trans-tibial amputation. The '165 patent added an outer socket 110 (FIG. 3 of the '165 patent), a pylon 126, and prosthetic foot. Thus, the post-operative protective socket 10 could be inserted into the outer socket with pylon and prosthetic foot attached to allow the amputee to stand and walk.

The post-operative preparatory socket 10 is designed with a rear shell 13. As stated in the '165 patent, "The rear shell 13 is brought to a higher elevation so it passes over the wearer's knee and covers a portion of the wearer's thigh above the knee." (Lines 2 to 4 of the '165 patent). Preparatory Socket 10 was designed to immobilize the knee during the initial recovery of the amputee. Movement of the knee after the operation before it has sufficient time to heat could result in a reopening of the wound and other complications.

The '165 patent further states:

After additional healing has occurred and the amputation is ready for full weight bearing, the patient will no longer need the post-operative preparatory socket 10. Instead, a supra patellar socket 210 is indicated (FIG. 2). (Column 5, lines 37 to 40)

The supra patellar socket 210 was designed to allow the knee to flex for full mobility when inserted into outer socket 110 with pylon 126 and prosthetic foot 130.

Although unique and very functional, the system described by the '209 and '165 patents still required three different sockets. Additionally, to accommodate a wide spectrum of limb sizes of amputees at least 5 different sizes of post-operative protective sockets 10 and supra patellar sockets 210 were needed. This is due to the limitation of adjustability of the sockets 10 and 210.

No admission is made that any reference cited herein constitutes prior art. Applicant expressly reserves the right to challenge the accuracy and pertinence of any cited documents.

SUMMARY

Among the objectives of the present invention is to provide an adjustable prosthetic system for an amputee that can be adjusted for changes in the size and condition of an amputee's limb during post-operative recovery and rehabilitation.

It is an objective of the present invention to provide an interface socket that can initially restrict movement of the leg of the amputee during post-operative recovery and then can be modified to allow movement of the amputee's knee joint.

It is an objective of the present invention to reduce the number of sockets needed to accommodate the varying leg sizes of amputees.

It is an objective of the present invention to provide a prosthetic system that can be modified and adjusted to meet the changing needs of a post-operative amputee during the recovery and physical therapy stages without the need to provide more than one set of sockets.

The invention accomplishes the above objectives and other objectives by providing an interface socket for a trans-tibial amputee having: a) a base cup; b) a lower back shell attached to the base cup by a flexible back strut; c) an upper back shell connected to a top edge of the lower back shell; d) a front shell connected to the base cup by a flexible front strut; e) wherein the interface socket is made of a flexible, resilient and formable material; and f) wherein the front shell and the lower back shell with the upper back shell attached are positioned to form a space there between to receive a limb of a trans-tibial amputee and be adjusted to vary the space there between to hold and grip the limb in a secure and comfortable fashion.

In another aspect of the interface socket the upper back shell is detachably connected to a top edge of the lower back shell and thus the upper back shell can be removed to allow the amputee to flex a knee of the amputated limb. In a further aspect of the interface socket of claim 2 wherein the detachable connection is selected from a group consisting of a) a super condylar super patellar trim line, b) a supra condylar trim line, and c) patellar tendon bearing trim line.

In a further aspect of the invention the interface socket: a) a first end of the back strut connects to the lower back shell at a point above a bottom edge of the lower back shell with a first set of open ended slots on either side of the back strut which slots open at the bottom edge of the Lower back shell and terminate at their opposite closed end where the first end of the strut connects to the lower back shell; b) a second end of the back strut connects to a bottom of the base cup with a second set of open ended slots on either side of the back strut, the second set of open ended slots are open at a rim of the base cup and terminate at a closed end adjacent to the connection of the second end to the bottom of the base of the cup; c) wherein the back strut has a bend in it that positions a plane formed by the base of the base cup approximately perpendicular to a plane formed by a line up a middle of the lower back shell; and d) wherein the structure allows the lower back shell to be moved in relation to the front sell to vary the space between the lower back shell and the front shell.

In a further aspect of the invention: a) the flexible front strut of the interface socket connects at a first end to a portion of a rim of the base cup opposite a bottom edge of the front shell; b) the flexible front strut of the interface socket connects at a second end to a portion of a bottom of the front shell with open ended slots on either side of the strut to thereby create a bottom edge of the front shell separated from and opposite from a portion of the rim of the base cup on either side of the front strut; and c) wherein the structure described allows for a flexing of side edges of the front shell to thereby allow the side edges of the front shell to slip inside of outside of edges of the lower back shell when the front shell and the back shell are moved towards each other to decrease the space therebetween.

In another aspect of the invention the flexible, resilient and formable material the interface socket is made from is polyethylene.

In yet another aspect of the invention it includes a lower socket for holding and supporting an interface socket, the lower socket consisting of: a) bottom cup; b) a front shell connected to a front top edge of the bottom cup; c) a back shell attached to the bottom cup by an articulated adjustable strut; d) wherein the lower socket is made of a flexible, resilient and formable material; and e) wherein the front shell and the back shell form an interior space to accept an interface socket and the space between the front shell and the back shell can be varied by movement of the articulated strut to accommodate post-operative interface sockets of varying sizes.

In yet another aspect of the invention the flexible, resilient and formable material the lower socket is made from is polypropylene.

In another aspect of the invention the articulated adjustable strut of the lower socket is hingedly and securely connected at a first end to the back shell and hingedly and securely connected at a second end to the bottom cup at a position opposite the front shell.

In yet another aspect of the invention the articulated adjustable strut of the lower socket has a center plate with a first plate hingedly attached at a first edge of the center plate and a second plate attached at a second edge of the center opposite the first edge, wherein the first plate is detachabley connected to the back shell and the second plate is detachably connected to the bottom cup.

In a further aspect of the invention the back shell of the lower socket has an upper shell detachably connects to the back shell, wherein when the upper shell is removed an amputee wearing the lower socket can flex the knee of an amputated limb wearing the lower shell.

Additional features and advantages will be set forth in the detailed description which follows, and in part will be readily apparent to those skilled in the art from the description or recognized by practicing the embodiments as described in the written description and claims hereof, as well as the appended drawings:

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification.

The drawings illustrate one or more embodiment(s), and together with the description serve to explain principles and operation of the various embodiments.

BRIEF DESCRIPTION OF THE DRAWINGS

FIG. 2A is a rear view of an embodiment of the post-operative interface socket showing the structure and connection of the posterior or rear strut among other things;

FIG. 2B is a view of the front of an embodiment of the post-operative interface socket showing among other things the structure of the front connecting strut;

FIG. 2C is a view of the bottom of the post-operative interface socket;

FIG. 6A is a schematic view of the right side of an embodiment of the post-operative interface shell of the present invention which depicts a supra condylar supra patellar (SCSP) connecting trim line;

FIG. 6B is a schematic view of the right side of an embodiment of the post-operative interface shell of the present invention which depicts a supra condylar (SC) connecting trim line;

FIG. 6C is a schematic view of the right side of an embodiment of the post-operative interface shell of the present invention which depicts a patellar tendon bearing (PTB) connecting trim line;

FIG. 8A is the same view as FIG. 8 but with the back shell of the lower socket at a fully open position;

FIG. 9 is a rear perspective view of an embodiment of the outer or Lower socket of the present invention;

FIG. 178 is a back view of the lower or outer socket with the articulated socket attachment installed; FIG. 20 is a side view of the single socket embodiment prosthetic system; and FIG. 21 is a side view of the single socket prosthetic system showing how the rear shell can pivot forward to accommodate changes in the size of the amputated limb during recovery;

DETAILED DESCRIPTION

Figure 1:
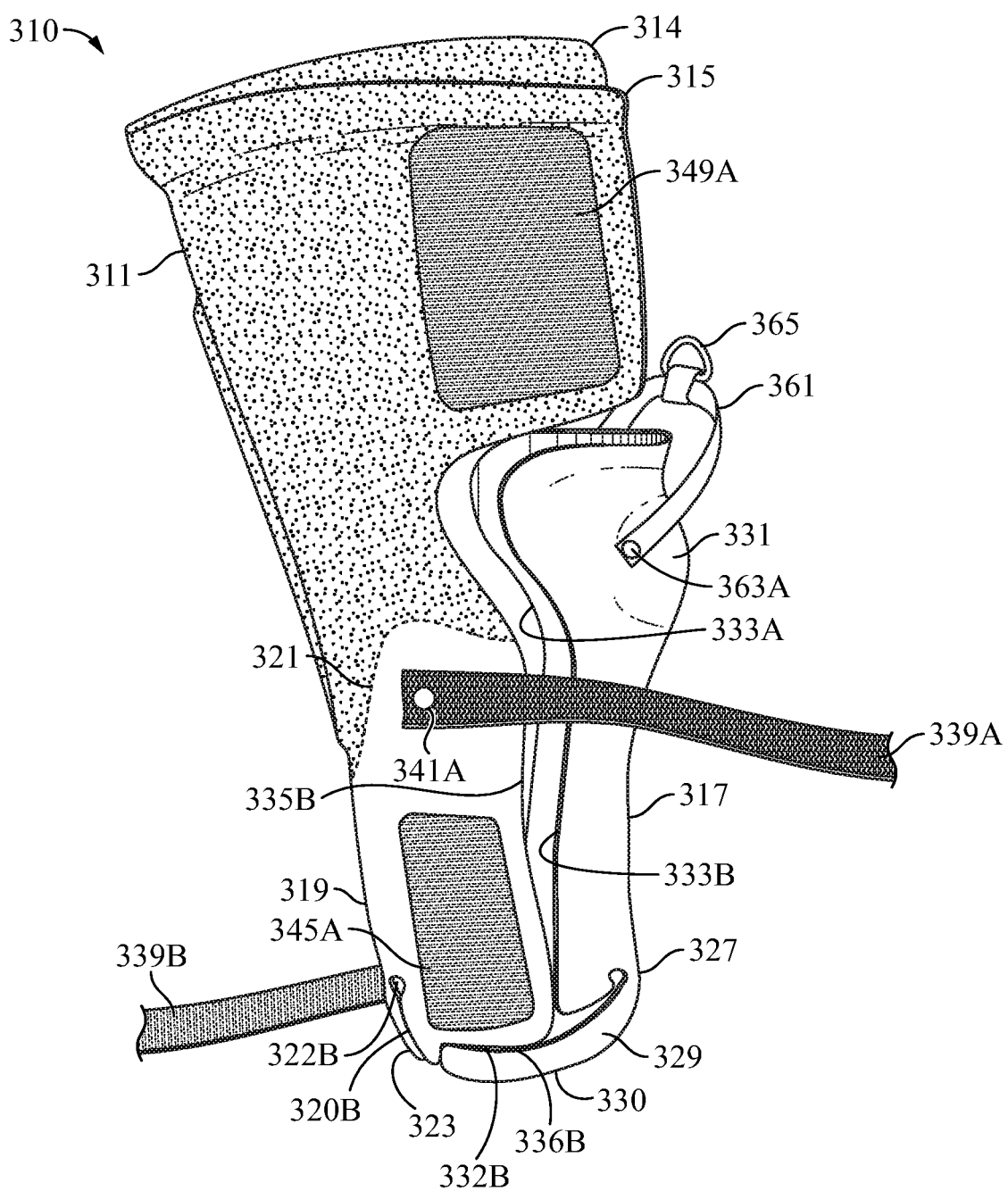
FIG. 1 is a side view of an embodiment of the post-operative interface socket of the present invention.

I The Post-Operative Interface Socket of the Perpetual Dimension Prosthetic System FIG. 1 provides a right side view of the post-operative interface socket 310 of the present invention. This is the interface socket that an amputees' leg will be inserted into shortly after undergoing a trans-tibial amputation. It includes the upper rear shell 311 with left side wing 314 and right side wing 315. (References to right and left herein are from the perspective of the amputee that would be using the prosthetic device, such as the amputee would be facing in the same direction as the front of the prosthetic apparatus faces. This is equivalent to the nautical terms of "port" for left side and "starboard" and for right side.)

The preferred embodiment of the system and apparatus of the present invention configures the prosthetic system for either the right or left leg, depending on which limb has the trans-tibial amputation. Some of the drawings in this application depict the system and apparatus configured for an amputee that has undergone a trans-tibial amputation of the left leg. However, those skilled in the art will readily understand that the prosthetic system and apparatus of the present invention can be easily configured for the right leg and that the version for the left or right legs are essentially mirror images of each other.

Also, in FIG. 1 tower front shell 317 and lower back shell 319 are visible. Upper rear shell 311 detachably connects to lower rear shell 319 along line 321. At its lower end tower back shell 319 connects by posterior or rear flexible strut 323 to base 330 of bottom cup 329. Front shell 317 connects to bottom cup 329 by front strut 327. Dome 331 provides space to accommodate the knee of the amputee.

As appears in FIG. 1 securing strap 339A connects by rivet 341A to the side of lower back shell 319 and a portion of securing strap 339A is visible, it attaches by rivet 341A (not shown in this drawing) to the side of tower rear shell 319. Hook fastener patch 349A is visible on right side wing 315. Hook fastener patch 345A is visible on lower rear shell 319. The full length of the straps are not shown just portions of the straps. In the embodiment of the invention disclosed herein the securing and connecting mechanisms, the straps, patches etc., used are a Velcro® like fabric hook and Loop connecting system, the hooks being one of the connecting surfaces and the loops on another. Reference will be made to fabric hooks and loop fasteners and will be referred to as the hook and loop fastener or individually as hook fastener or loop fastener. Alternatively, they may be simply referred to as a securing straps or patches. It is noted that any other type of fastener or securing system that can accomplish the same functions can be used.

Figure 2:
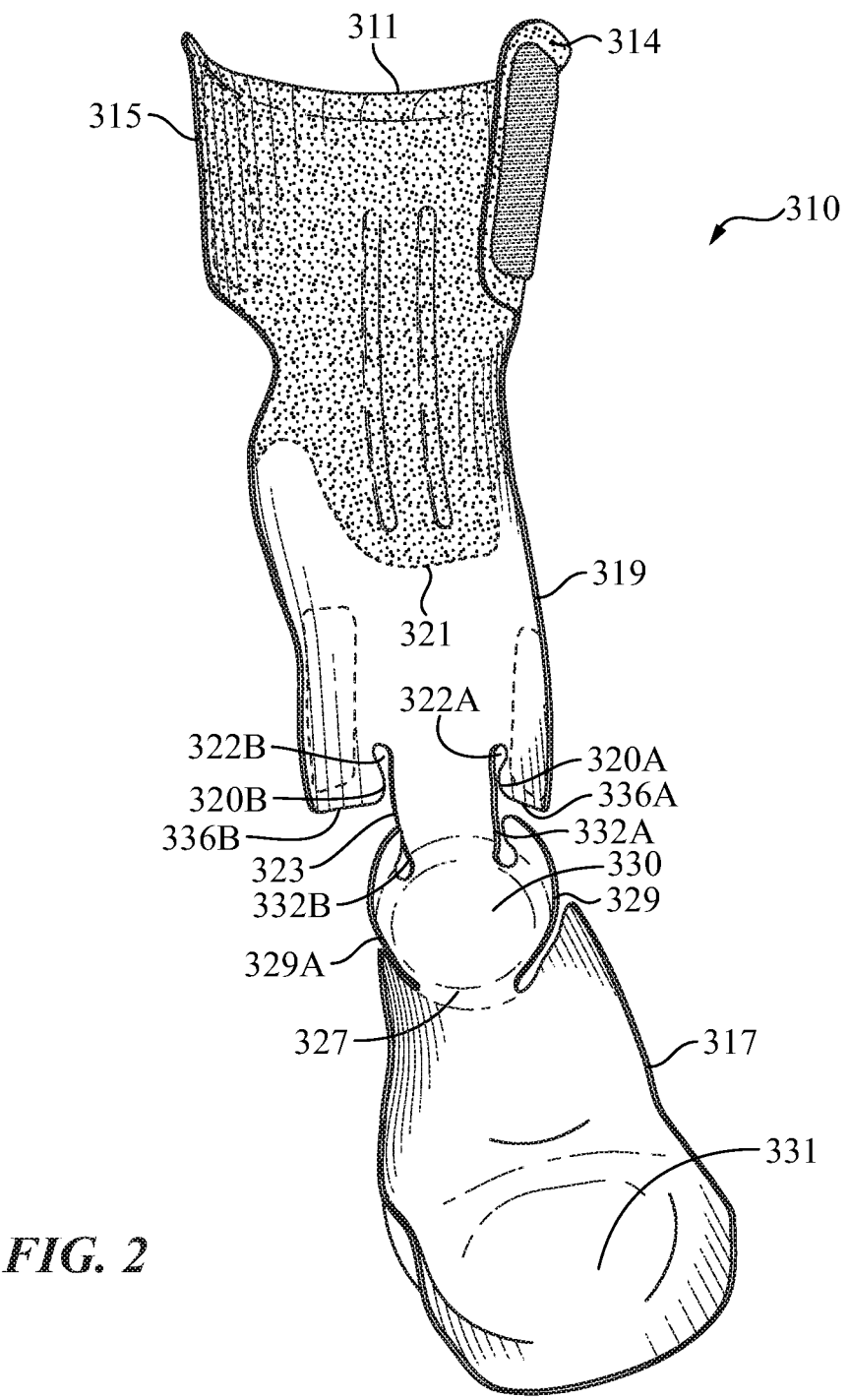
FIG. 2 is a top view of an embodiment of the post-operative prosthetic socket with the front and rear shells spread apart.

FIG. 2 provides a view of the post-operative interface socket 310 of the present invention with front shell 317 and rear lower shell 319 upper rear shell 311 combination spread out for illustrative purposes. Lower back shell 319 connects to the base 330 of bottom cup 329 by posterior or rear flexible strut 323. Front shell 317 connects to bottom cup 329 by front strut 327, Dome 331 provides a space to accommodate the amputee's knee. FIG. 2 also demonstrates the fact that interface socket 310 is made out of a very flexible but resilient material. In the embodiment depicted polyethylene is the preferred material, but any similar material that has the same qualities can be used.

FIG. 2A is a view of the posterior or rear of post-operative interface socket 310. Upper rear shell 311 detachably connects along line 321 to lower rear shell 319 and back rear flexible strut 323 connects lower rear shell 319 to bottom cup 329. Hook patches 345A and 345B are visible on lower rear shell 319. As noted, above the version of the post-operative interface socket 310 depicted is for the left leg. As noted posterior or rear flexible strut 323 connects to base 330 of bottom cup 329 at one end and it connects at its opposite end to lower rear shell 319.

For another view we refer to FIG. 2C, a bottom view of post-operative interface socket 310, where open ended slots 328A and 328B eliminate the need for strut 327 to connect to rim 329A of cup 329 and thus can bypass it and attached to bottom 330 of cup 329. By varying the length of slots 328A and 328B the actual connection of strut 323 to base 330 can be made at any selected spot. Open ended slots 328A and 328B end in circular apertures 325A and 325B. The circular apertures 325A and 325B along with slots 328A and 328B add greater flexibility to the system to vary the distance between front shell 317 and lower rear shell 319 which will be discussed below.

Referring back to FIG. 2A rear flexible strut 323 does not connect to the bottom edges 336A and 336B of lower back or rear shell 319 rather as a result of open ended slots 320A and 320B strut 323 attaches further up to lower back shell 319. Here again the length of slots 320A and 320B can be varied to allow the actual point of connect of strut 323 to lower rear shell 319 to be at any desired position on lower back shell 319. Open ended slots 320A and 320B end in circular apertures 322A and 322B. Additionally slots 332A and 332B separate cup 329 from bottom edges 336A and 336B of lower back shell 319. The unique structure described above allows for the movement of lower back shell 319 with respect to front shell 317 to thereby allow of the adjustment of the space between the front shell and the lower back shell and thus accommodate amputated limbs of varying sizes and well as changes in the size or circumference of an amputee's limb that occur overtime during the recovery process as will be discussed further below.

Referring to FIG. 28 an anterior or front view of post-operative interface socket 310. Front shell 317 connects by front connecting strut 327 to cup 329. Front strut 327 connects front shell 317 to rim 329A of bottom cup 329. Strut 327 is narrower than front shell 317, there being open ended slots 326A and 326B on either side of strut 327 that separate and create a space between rim 329A of bottom cup 329 and bottom edges 316A and 316B of front shell 317. Each open ended slot 326A and 326B terminates respectively in circular apertures 334A and 334B. Front shell 317 has side edges 333A and 3338. Also, visible in FIG. 2B are side edges 335A and 335B of lower back shell 319. As will be discussed below given the structure described in this paragraph and depicted in FIG. 2B the side edges 333A and 333B of front shell 317 can be inserted inside of side edges of 335A and 335B of lower back shell 319 to provide an additional means for adjusting the distance between front shell 317 and lower rear shell 319 to vary the space between them and accommodate limbs of different size and also to accommodate changes in the size of the amputated limb held. One of the features of the slot structure and front strut 327 is that it allows for the bending of edges 333A and 333B of front shell 317 to fit inside of edges 335A and 335B to allow for adjusting the space between front shell 317 and lower rear shell 319 by allowing the front shell to slip inside of the lower rear shell.

As noted in a preferred embodiment, post-operative interface socket 310 is made of polyethylene or some similar flexible but durable formable material. Also, in the embodiment depicted, its thickness is approximately 2 to 3 millimeters.

Figure 3:
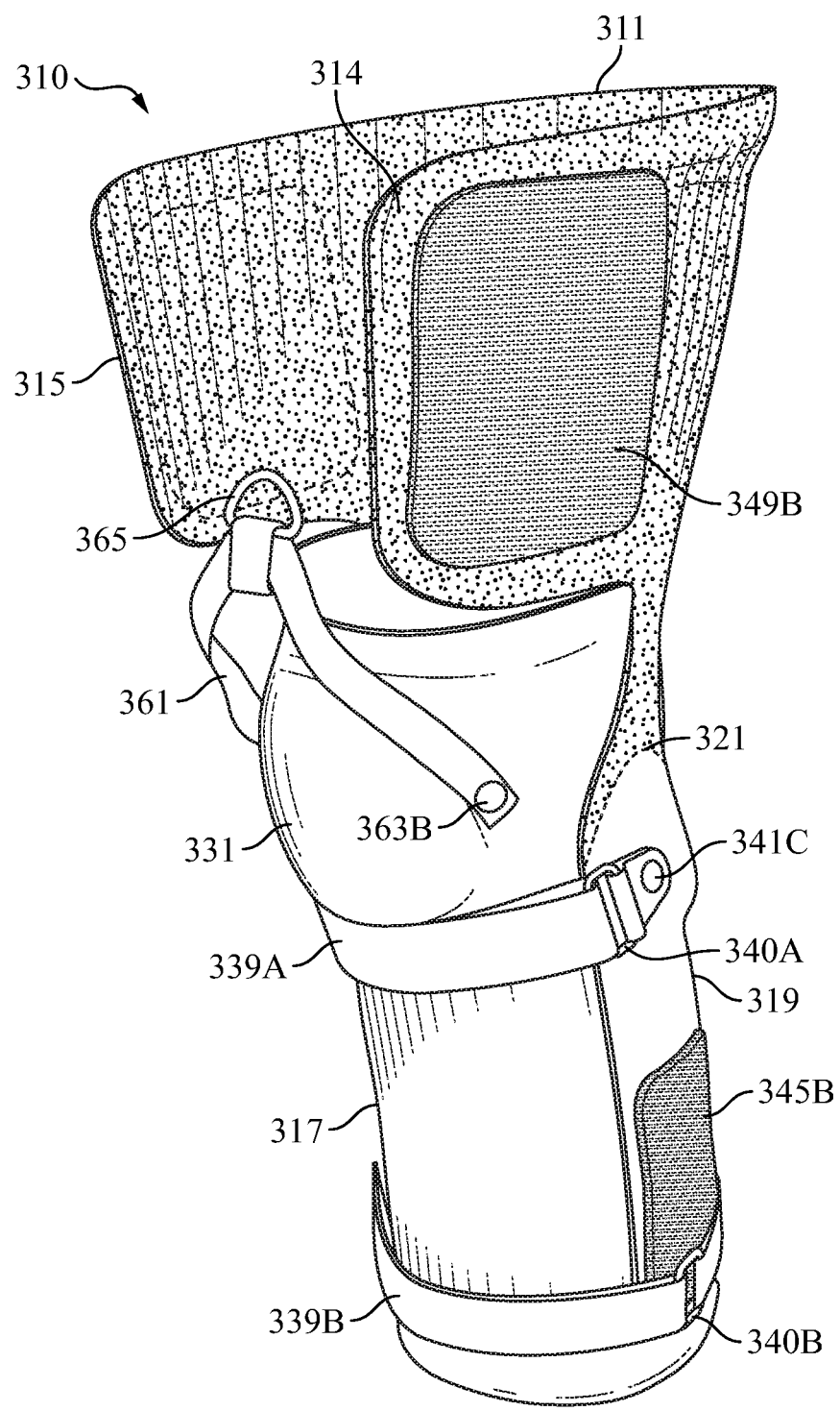
FIG. 3 provides a front left side view of an embodiment of the post-operative interface socket.

FIG. 3 provides a front left side perspective view of post-operative interface socket 310 of the present invention. In this view straps 339A and 339B have been secured around front shell 317. Strap 339A has been looped through metal loop 340A and then secured back on itself with hook and loop connectors it has on opposing surfaces. Loop 340A being secured by rivet and fabric strap 341C. Likewise strap 339B has been secured around front shell 317. Strap 339B has been looped through loop 3408 and then secured back on itself with hook and loop connectors it has on opposing surfaces. As depicted in FIG. 2A strap 339B is connected to the back of lower rear shell 319 by rivet 341B. Referring back to FIG. 3 Strap 361 is secured at one end by rivet 3638 and metal and metal loop 365 is at the center of strap 361. Hook securing patch 349B is on the outside of left side wing 314 of upper rear shell 311. Hook securing patch 345B is on lower rear shell 319. It should be noted that strap 339B is covering the slots on lower rear shell 319 and front shell 317 so they are not visible.

Figure 3C:
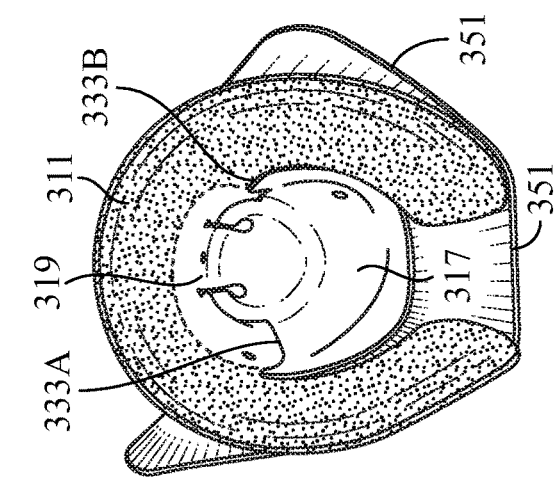
FIG. 3C provides a top view of an embodiment of the post-operative interface socket in its fully constricted position.
Figure 3B:
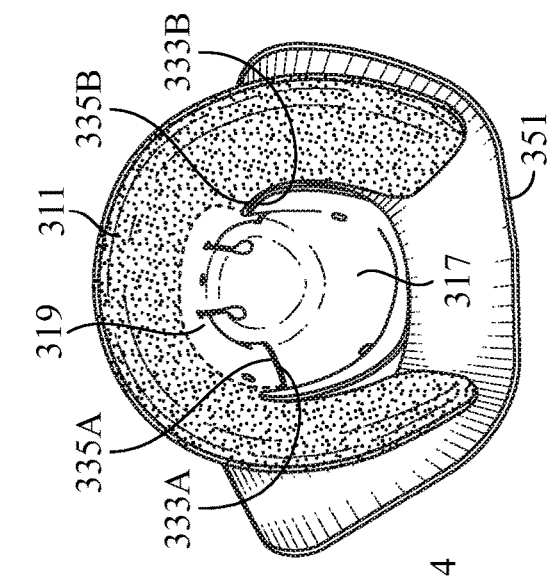
FIG. 3B provides a top view of an embodiment of the post-operative interface socket in its intermediate closed position.
Figure 3D:
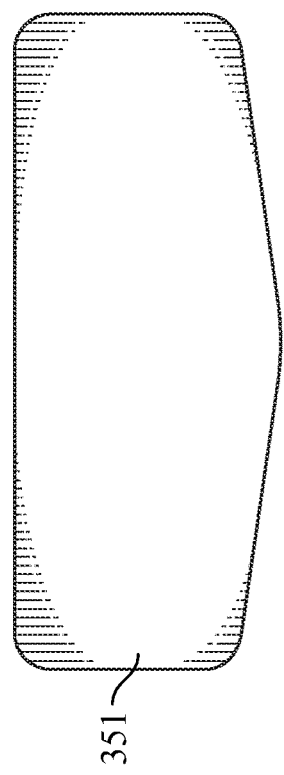
FIG. 3D is a view of a loop connecting pad laid out.
Figure 3A:
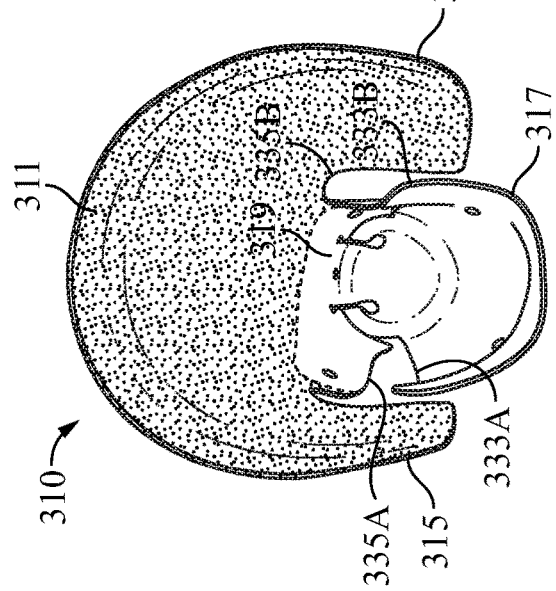
FIG. 3A provides a top view of an embodiment of the post-operative interface socket in its fully open or dilated position.

FIGS. 3A, 38 and 3C are top views of the post-operative interface socket 310 that depict the variations of its interior diameter, which can vary to accommodate limbs of varying size and also adjust for swelling or decrease in the size of a limb that normally occurs during the post-operative recovery period.

FIG. 3A provides a top view of post-operative interface socket 310 in the fully open position with the edges 333A and 333B of front shell 317 separated from edges 335A and 335B of lower back shell 319. In FIG. 38, the interior diameter formed by front shell 317 and lower rear shell 319 is decreased and with the edges 333A and 333B of front shell 317 abutting against edges 335A and 335B of front shell 317 abutting against edges 335A and 335B of lower bottom shell 319. In FIG. 3C edges 333A and 333B of front shell 317 have slipped inside of shell 319 further reducing the interior diameter of post-operative interface socket 310. The edges of lower rear shell 319 are not visible because they are covered by the sides of front shell 317. Also in FIG. 3B loop securing patch 351 has been attached to hook securing patches 349A and 349B (patches 349A and B are visible in FIGS. 1 and 3). Attaching loop securing patch 351 allows one to reduce the curvature of wings 315 and 314 of upper rear shell 311. In FIG. 3C patch 351 has been attached and wings 315 and 314 have been further constricted, FIG. 3D provides a view of fabric loop securing patch laid out.

Figure 4:
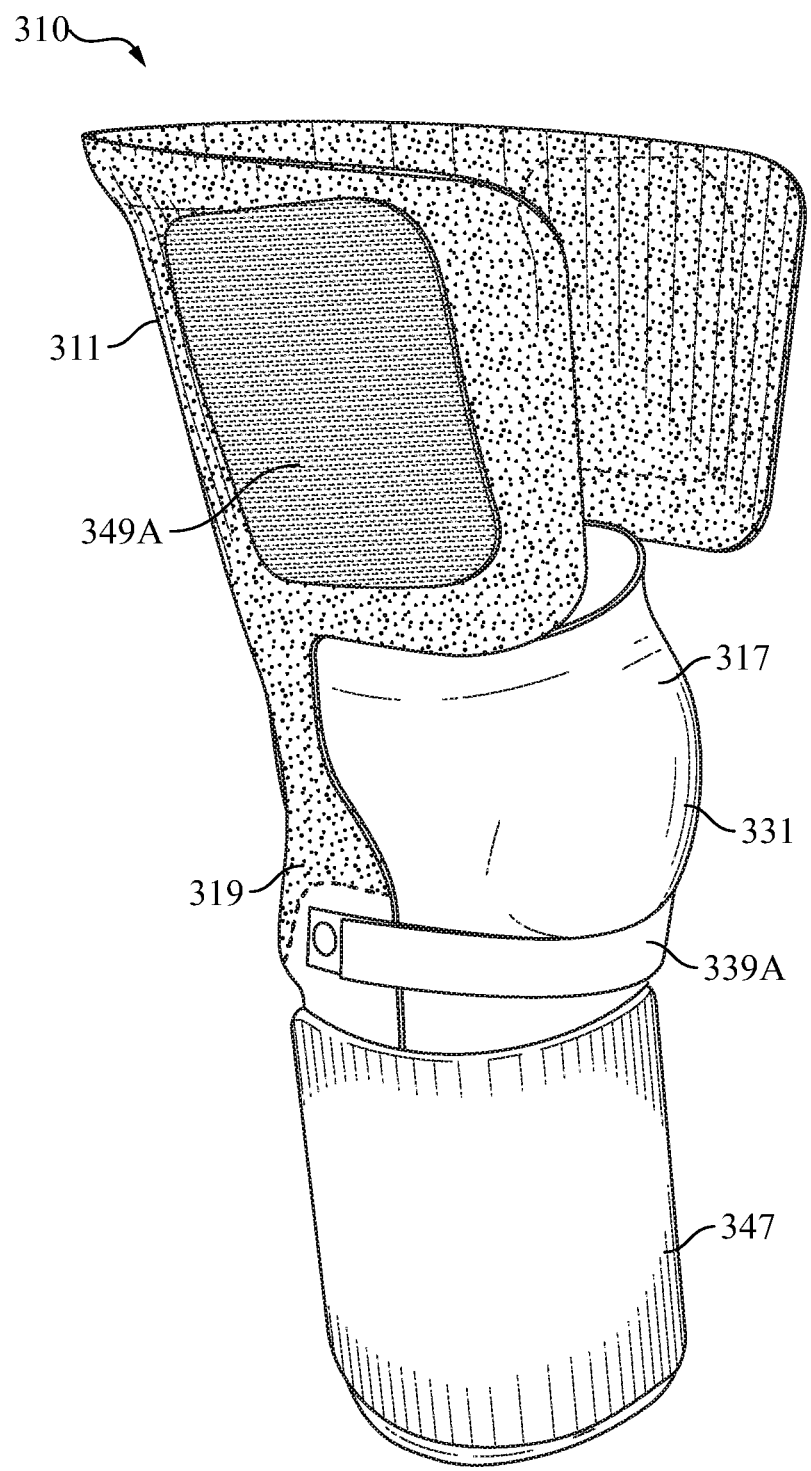
FIG. 4 provides a side perspective view of an embodiment of the post-operative interface socket with securing devices attached, including a loop connecting pad.

FIG. 4 is a right (starboard) slightly raised side perspective view of the post-operative interface socket of the present invention with securing devices attached. Strap 339A is secured around front shell 317 and loop securing patch 347 is attached to hook patches 345A and 345B securing it around front shell 317. Hook patches 345A and 345B are visible in FIGS. 1 and 3. Strap 339B is not visible since it is covered by patch 347.

Figure 6:
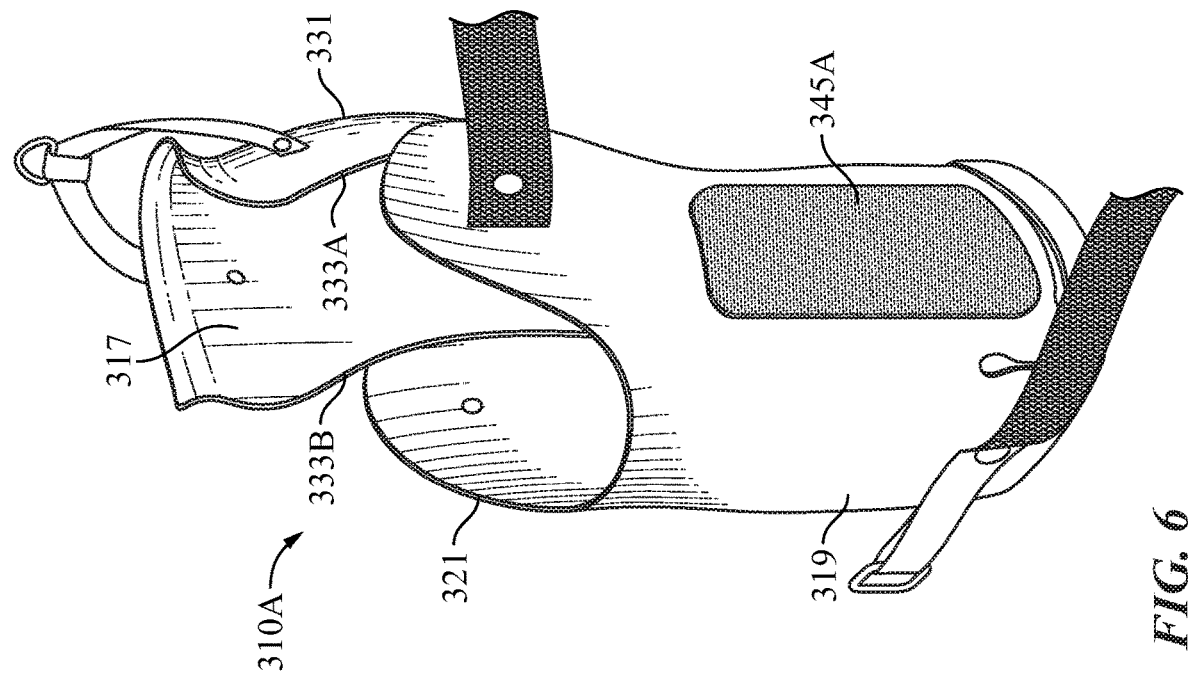
FIG. 6 is a rear right-side view of an embodiment of the post-operative interface socket with the upper rear shell removed.

Referring to FIGS. 1, 2 and 2A connecting line 321 along which upper rear shell 311 which is a detachable connection to lower rear shell 319 is in effect a trim line. The type of trim line depicted in FIG. 5 and FIG. 6 after upper rear shell 311 is removed is a supra condylar supra patellar (SCSP) trim line. Note that upon removal of upper rear shell 311 the interface socket is identified by reference number 310A in this specification. However, the trim line can be varied depending on the needs of the particular amputee. FIGS. 6A, 6B and 6C provide a schematic diagram of some of the various trim lines that can be achieved with the present invention. In FIGS. 6A, 6B and 6C the hatched area in each figure is the portion of post-operative interface shell 310 namely upper rear shell 311 that is removed after the amputee's leg has sufficiently healed such that the leg and specifically the knee no longer needs to be immobilized and it becomes interface socket 310A.

FIG. 6A is an SCSP trim line wherein upper rear shell 311 is removed along SCSP trim line 321. As can be seen only upper rear shell 311 is removed. FIG. 6B depicts a supra condylar (SC) trim line 321A wherein not only is rear shell 311 detached along line 321A but trim line 321A continues along the top of front shell which is also removed. FIG. 6C shows a patellar tendon bearing (PTB) trim line 3218 where upper rear shell 311 is detached from lower rear shell 319 along line 321B, and trim line 321B continues along front shell 317 to thereby remove a significant portion of front shell at and below where the knee of the amputee would be when the amputee is wearing the post-operative interface socket 310A.

As demonstrated in FIGS. 3A, 3B and 3C above by use of straps 339A and 339B the interior diameter of post-operative interface socket 310 can be varied as depicted in FIGS. 3A, 3B, and 3C. By placing security hook fastener patch 347 around front shell 317 connected to patches 345A and 345B, this provides an additional means for securing a desired or required inner space in post-operative interface socket 310 and to adjust it to the varying size of the post-operative trans-tibial amputated limb.

The ability to vary the interior circumference of post-operative interface socket 310 and likewise 310A, after removal of upper shell 311, provides a number of advantages. First, it reduces the number of sizes of post-operative interface sockets 310 that need to be maintained in stock to accommodate amputee limbs of varying size. The flexibility in sizing described above increases the dimensional range of the anterior-posterior (AP) range and medial-lateral (ML) and circumferences from 4" to 6" depending on the size of the patient. Additionally, the circumference of the portion of amputated limb will vary significantly from the time of the operation amputating the lower limb to the time the amputee is able to walk normally. Right after the operation, the limb will typically swell due to the trauma of the surgery. While recovering from the operation and healing, the amputee's limb will shrink in diameter as part of the healing process as well as the relative inactivity imposed on it. This is in part due to the need to keep the knee immobilized during the initial recovery phase. Post-operative interface socket 310 can be easily adjusted by straps 339A and 339B and patch 347.

Figure 5:
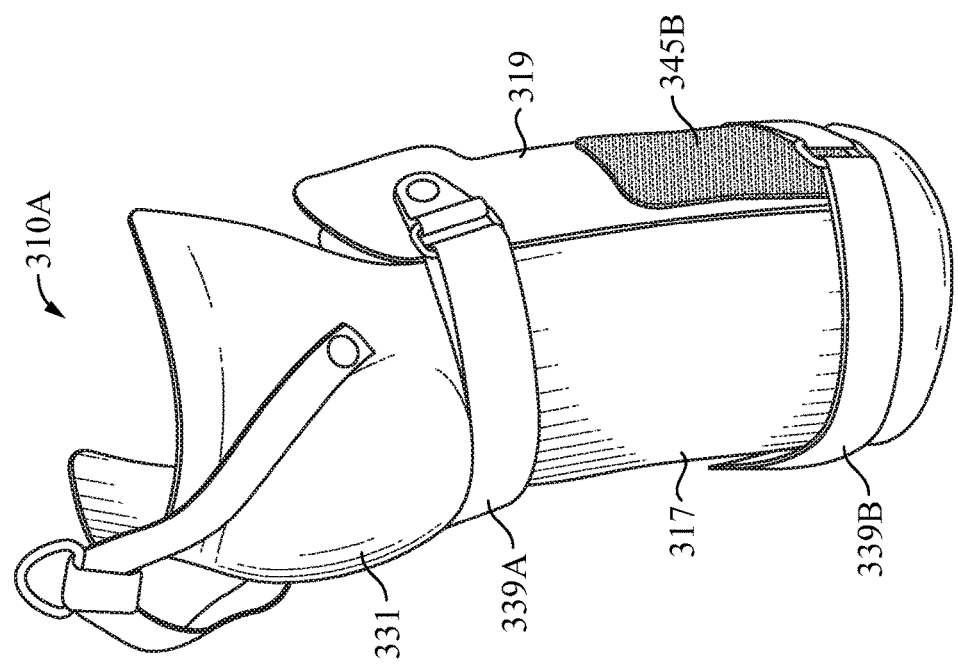
FIG. 5 is a front left side view of an embodiment of the post-operative interface socket of the present invention with the upper rear shell removed.

Once the initial healing process is complete and the patient can start flexing their knee, there is no need to switch to another interface socket. As depicted in FIG. 5, upper back or rear shell 311 is detached from lower back shell 319 along line 321. This then allows the amputee to continue to use post-operative interface socket 310A and start to flex his or her knee. Upper back shell 311 when attached to lower back shell 319 is designed to immobilize the limb and prevent flexing of the knee to aid in the initial heating process. However, once the healing process has progressed sufficiently the amputee needs to start flexing the knee to begin the process of starting to walk and move normally. FIG. 6 provides a rear view of post-operative interface socket 310A with upper rear shell removed so the amputee can flex their knee and bend their leg.

II The Outer or Lower Socket of the Perpetual Dimension Prosthetic System

Figure 8:
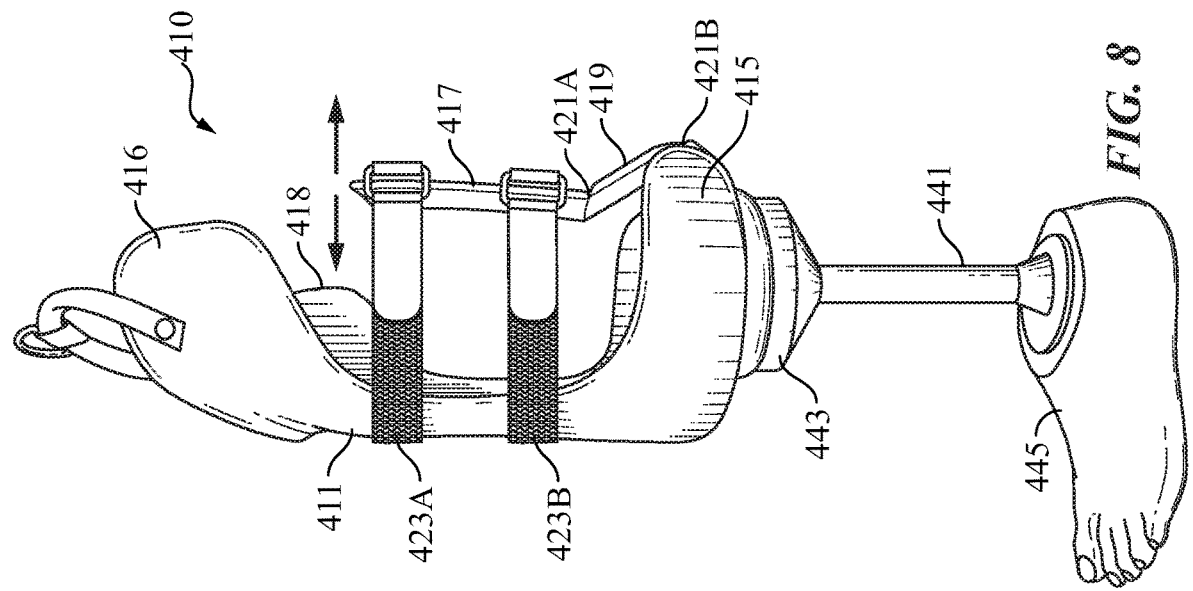
FIG. 8 is a side perspective view of an embodiment of the outer or Lower socket of the present invention in a constricted position.
Figure 7:
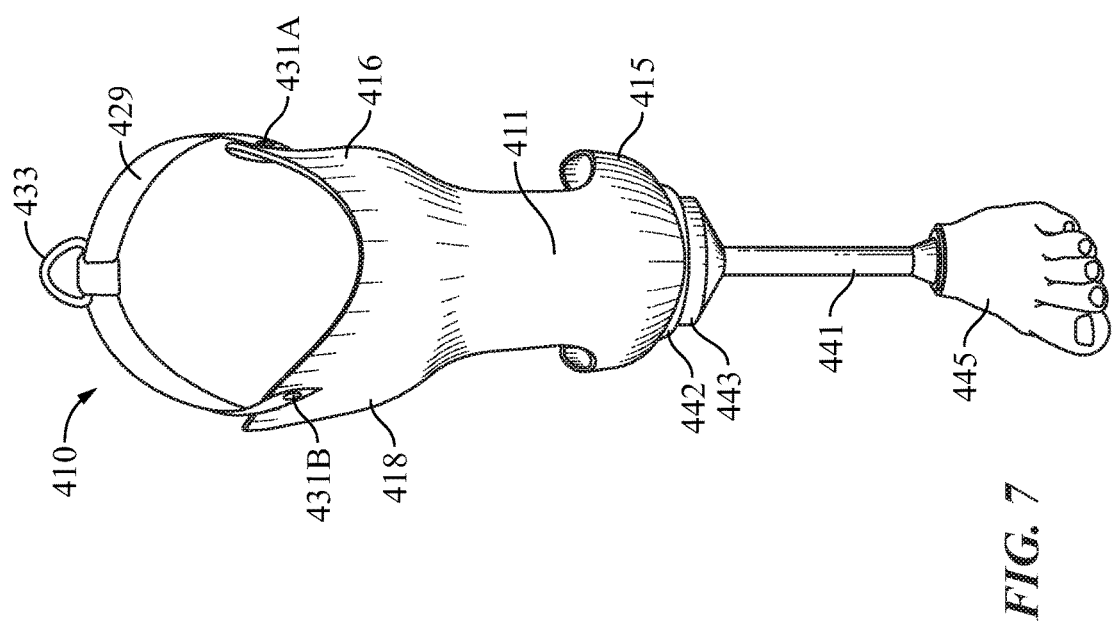
FIG. 7 is a front view perspective view of an embodiment of the outer or tower socket.

Outer or lower socket 410 is depicted in FIGS. 7, 8 and 9 in a front view, side view and rear view respectively. In a preferred embodiment polypropylene is the preferred material for outer socket 410. It provides a flexible, sturdy, resilient, formable and lightweight material. In the embodiment shown the thickness of the material is about 4 to 5 millimeters.

The parts visible in FIG. 7 include front shell 411, which attaches to base or bottom cup 415. Front shell 411 has a left wing 416 and a right wing 418. (As noted previously references to right and left herein are from the perspective of the amputee that would be using the prosthetic device, such as the direction the front of the object described faces. This is then equivalent to the nautical terms of "port" and "starboard".) Strap 429 connects to wing 418 by rivet 431B and to wing 416 by rivet 431A. Retention ring 433 is attached to the center of strap 429. Attached to the bottom receiving plate 442 which forms a reinforced base of bottom cup 415 is hardware connecting device 443, shaft 441 and artificial foot 445. In a standard fashion bolts, not shown would pass up through hard connecting device 443, through receiving plate 442 and connect to a retention bracket on the inside of bottom of outer socket 410. Shaft 441 securely attaches in a standard fashion to connecting hardware device 443. The connection created is strong enough to bear the weight and stress and strain of an adult waking the prosthetic system. Artificial foot 445 completes the system.

FIG. 8 provides a side view of lower or outer socket 410. In this side view additional parts of outer or lower shell are visible, namely back shell 417 and articulated strut 419 that connects to back shell 417 at flex line 421A and to base cup 415 at flex line 421B. Securing straps 423A and 423B connect around front shell 411 and hold back shell 417 in position.

FIG. 9 is a rear view of outer socket 410 without items 443, 441 and 445 attached. Additional aspects of lower socket 410 visible are flex lines 421A and 421B that allow articulate strut 419 to move back and forth. Rivet 427A holds strap 423A to back shell 417 and rivet 427B holds strap 423B to back shell 417. Rivet 424A holds metal loop and retention strap 425A and rivet 424B holds metal loop and retention strap 425B to back shell 417.

Flex lines 421A and 421B in the embodiment depicted in FIG. 9 are created by compressing the material which lower socket 410 is made of, in the embodiment depicted polypropylene. Flex lines 421A and 421B by movement of articulated strut 419 allow back shell 417 to be moved between the positions depicted in FIG. 8 and FIG. 8A and thus allow outer socket to adjust to the varying circumferential sizes the post-operative interface socket 310 will varying given the different in limb sizes of amputees and the variation of a particular amputees limb that occurs during the heating and recovery process.

Figure 16A:
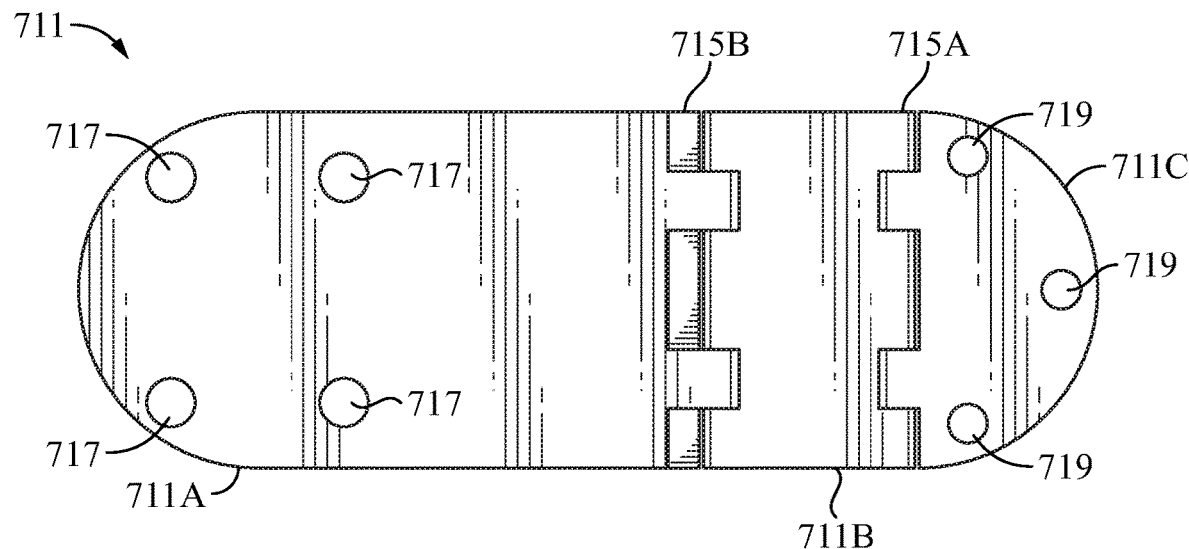
FIG. 16A a top or plan view of an articulated socket attachment plate system.
Figure 16B:
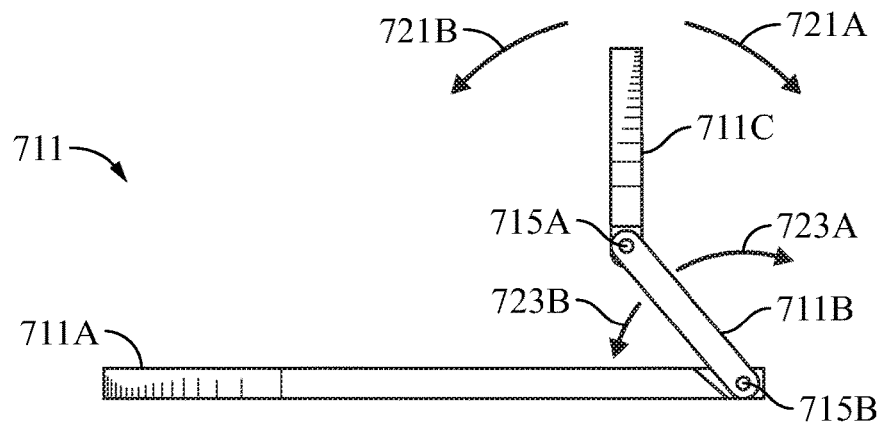
FIG. 16B a side view of an articulated socket attachment plate system.

FIG. 16A depicts another variation of the articulated and movable strut (419 depicted in FIGS. 8, 8A and 9). In the variation depicted in FIG. 16A is a separate double hinged socket attachment plate 711. Hinged socket attachment 711 is made up of a lower plate 711A, a middle plate 711B, and an upper plate 711C. Lower plate 711A connects to middle plate 711B by hinge 7158. Middle plate 711B connects to upper plate 711C by hinge 715A. Referring now to FIG. 16B a side view of articulated socket attachment plate 711. As depicted in FIG. 168, both hinges 715A and 7158 are fully articulated allowing the plates to be freely moved with respect to each other. As depicted plate 711C can be pivoted on hinge 715A with respect to plate 711B in the direction of arrows 721A and 7218. Likewise, plate 711B can be pivoted on hinge 7158 with respect to its orientation to plate 711A in the direction of arrows 723A and 7238. Plate 711 can be fabricated from any number of rigid but durable materials including aluminum, polypropylene, polyethylene, stainless steel, etc. . . . . . Screw holes 717 on plate 711A and screw holes 719 on plate 711C provide means for attaching articulated socket attachment 711 to the base cup and the back shell of the outer or lower socket, as will be described below.

Figure 17C:
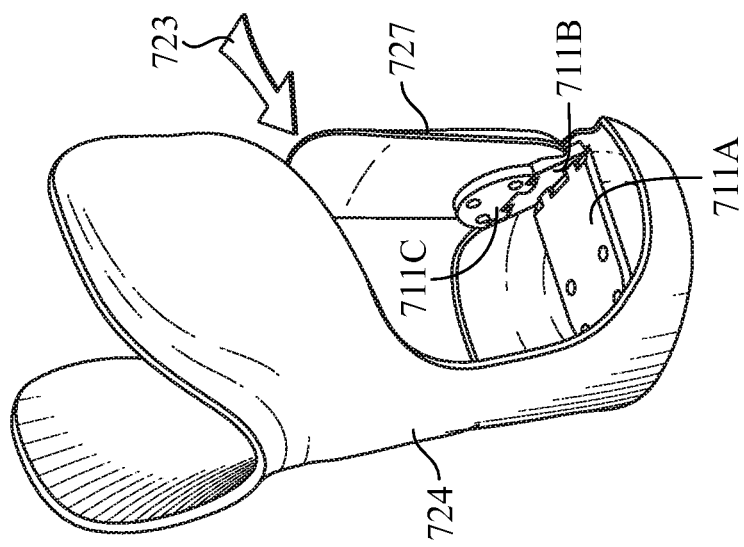
FIG. 17C is a side view of the lower socket and its rear shell positioned to accommodate a reduction in size of the upper interface socket.
Figure 17B:
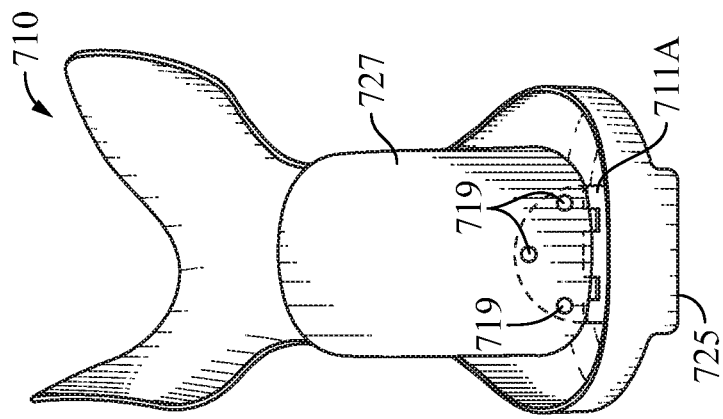
FIG. 17A is a side raised view of the lower or outer socket with the articulated socket attachment installed.
Figure 17A:
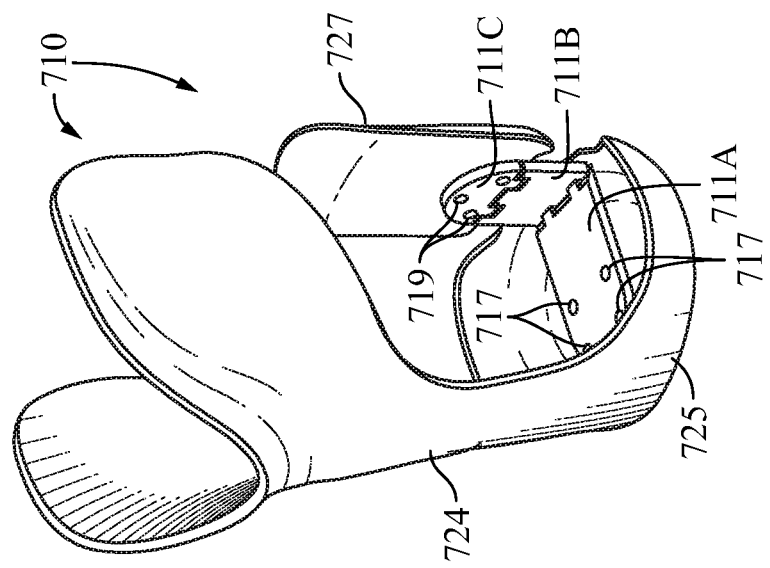

Referring now to FIG. 17A a side raised view of the lower or outer socket 710 with articulated socket plate system 711 attached to the lower or outer socket. As depicted, lower socket attachment plate 711A is attached to the top inside of base cup 725 of the lower socket. Plate 711A is attached in the standard fashion with screws inserted through screw holes 717. Plate 711C is attached to back shell 727, as depicted, in the standard fashion by inserting screws through screw holes 719. In this variation of the lower socket back shell is separate from the rest of the lower socket and only connected by the articulated socket attachment plate 711.

FIG. 178 is a rear view of tower socket 710 with articulated plate system 711 attached. As can be seen, back shell 727 is not directly attached to lower cup 725. Rather, articulated plate system 711B connects lower cup 725 to back shell 727. This is to allow for movement of back shell 727 to vary the size of space lower socket 710 provides. It thus serves the same function as articulated strut 417. FIGS. 8 and 8A show how articulated strut 417 allows for the varying of the distance between back shell 417 and the front of lower socket 410. FIG. 17C depicts how rear shell 727 can be moved forward by adjusting plates 711C and 711B with respect to 711A. This thus allows lower socket 710 to accommodate the varying size of the upper interface socket 310 as the trans-tibial amputee proceeds through the recovery process.

Figure 11:
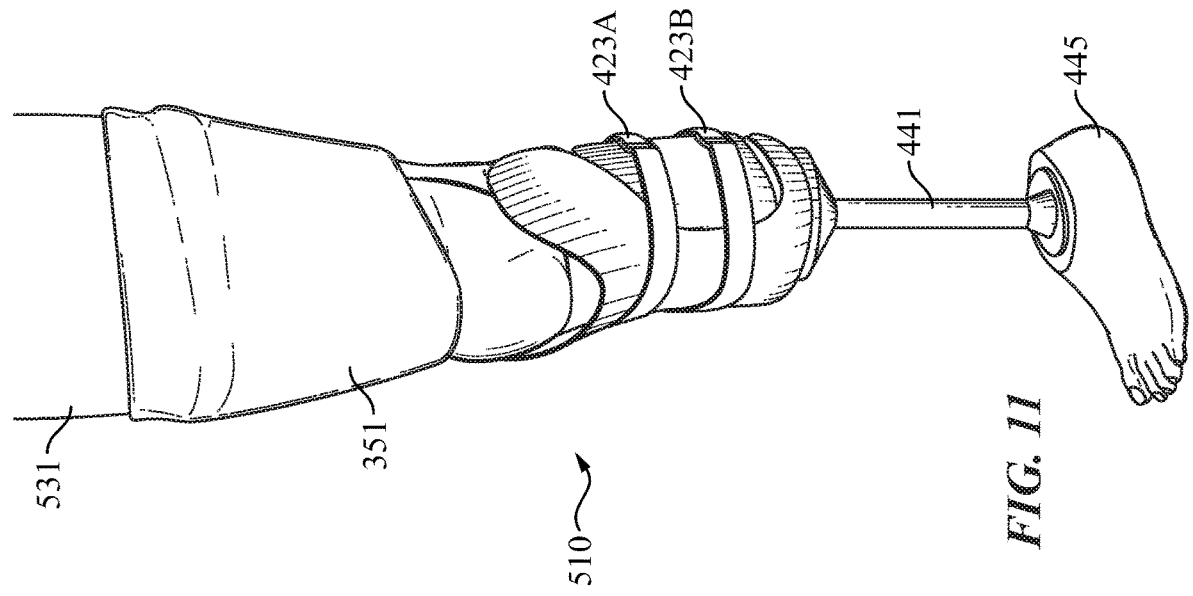
FIG. 11 is the same view as FIG. 10 with the addition of a securing patch and an amputee's leg visible.
Figure 10:
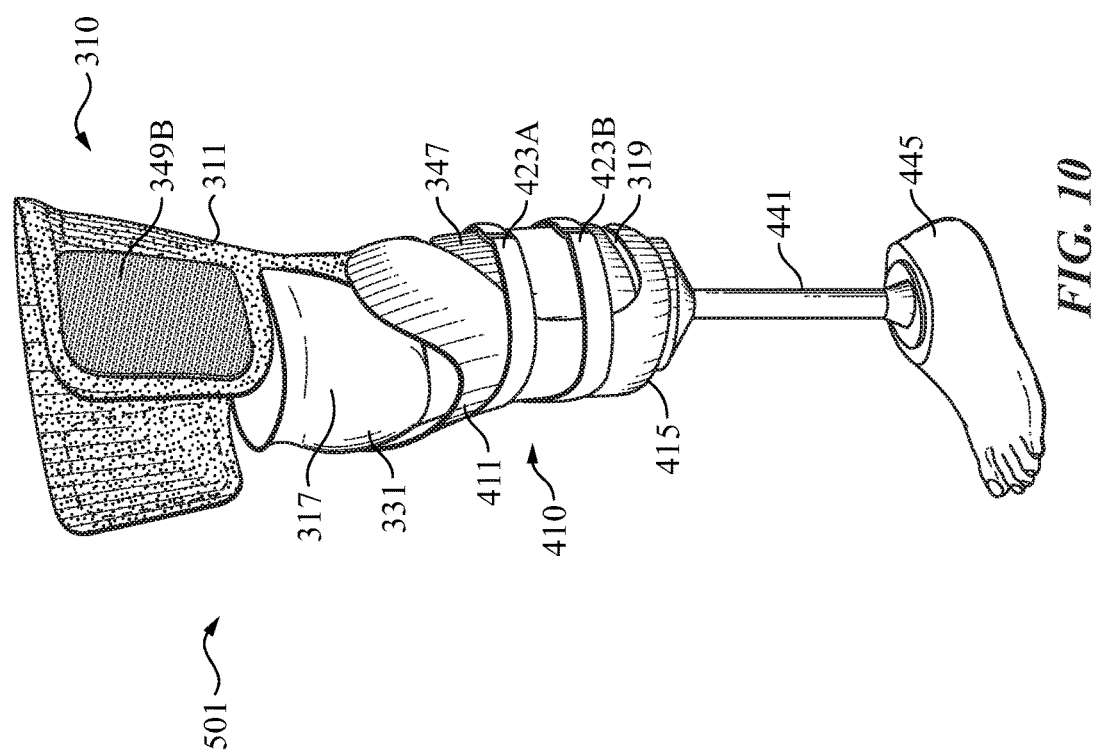
FIG. 10 is a slightly raised perspective front left side view of an embodiment of the combined post-operative interface socket and tower or outer socket system as they would appear connected.

III The Over All Combined Post-Operative Lower Socket Perpetual Dimension Prosthetic System FIG. 10 provides a front left side prospective view of the parts of the prosthetic system 501 of the present invention namely post-operative interface socket 310 as it is used with outer lower socket 410. Post-operative interface socket 310 is positioned inside of outer socket 410 with shaft 441 and artificial foot 445 attached in a configuration ready for a trans-tibial amputee to use. FIG. 11 provides a front left side perspective view of the prosthetic system 501 of the present invention as it might appear on an amputee's leg 531. The limb 531 of an amputee can be seen and loop patch 351 has been attached to hook pads 349A and 349B. AS depicted in FIG. 11 upper rear shell 311 immobilizes the limb 531 and prevents it from flexing at the knee. However, as pictured in FIG. 12, a rear left side view of the entire prosthetic system 501, upper rear shell 311 has been removed to allow limb 531 to flex at the knee as depicted therein.

Figure 13:
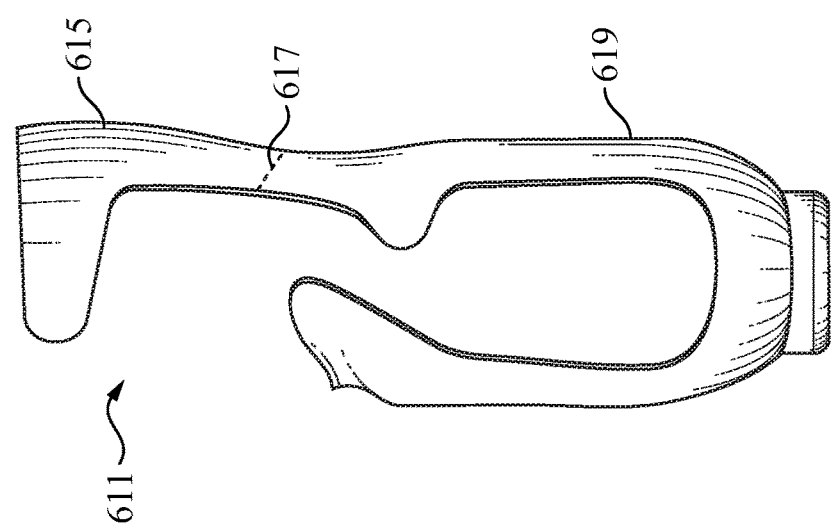
FIG. 13 is a side view of an alternative embodiment of the outer or lower socket of the present invention.

FIG. 13 provides a side view of an alternative version of the tower socket 611. In this variation of the invention lower socket 611 has a detachable upper back shell 615 detachable along line 617. Detachable upper back shell 615 has the same purpose as the detachable upper back shell 311 of the upper or interface socket 310, FIG. 1. Referring back to FIG. 13 upper back shell 615 of lower socket 611 is also designed to immobilize the trans tribal leg amputee's and prevent flexing of the knee during the initial heating process after the amputation. As noted previously the knee of the amputee needs for a period of time after the amputation to recover from the trauma of the operation.

Figure 12:
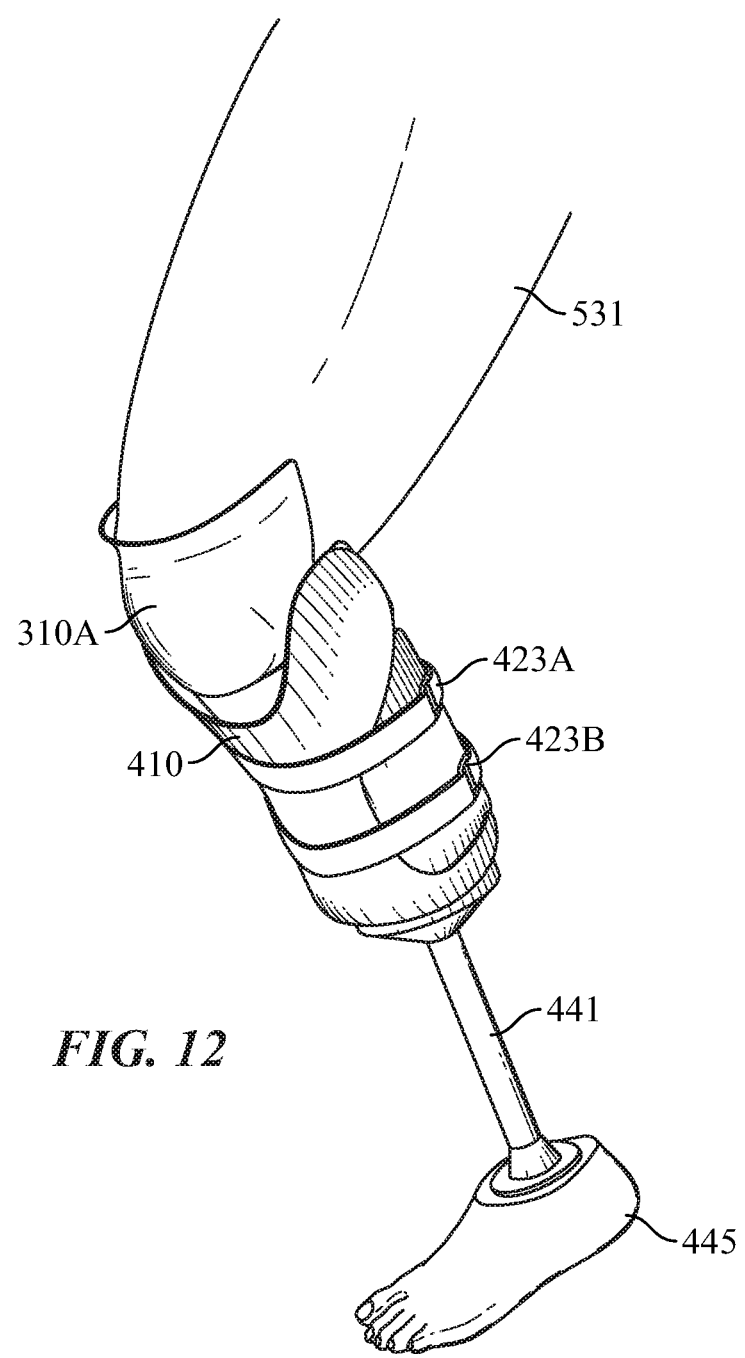
FIG. 12 is a left side view of an embodiment of the combined post-operative interface socket and lower or outer socket with the upper rear shell removed from the lower rear shell of the post-operative interface socket to thereby allow the knee of the amputee to flex and bend.
Figure 14:
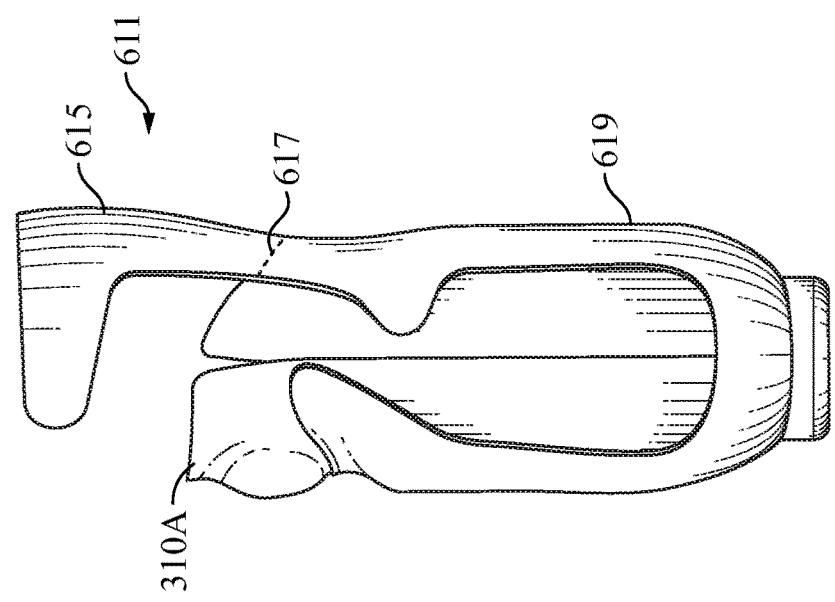
FIG. 14 is a is a side view or outer or lower socket depicted in FIG. 13 holding the upper post-operative interface socket that does not have an upper back shell.

FIG. 14 provides a side view of lower shell 611 of lower socket 611 holding post-operative interface socket 310A. In this variation depicted upper back shell 615 of lower socket 611 takes the place of upper rear shell 311 of interface socket 310. Once the amputee has sufficiently recovered upper shell 615 is removed along line 617. Once this upper shell 615 is removed the amputee then can flex his or her knee as depicted in FIG. 12.

Figure 15:
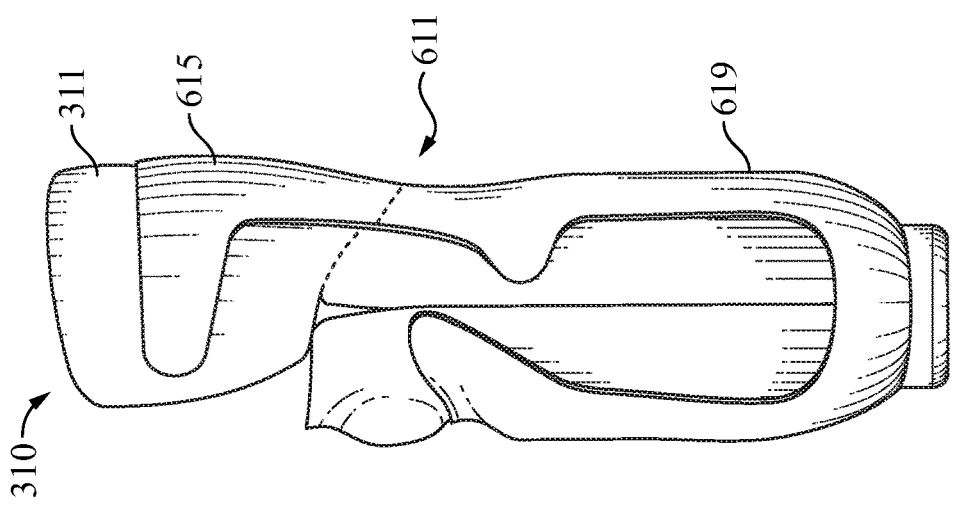
FIG. 15 is a side view of the lower socket of FIG. 13 holding a post-operative interface socket with an upper back shell.

FIG. 15 provides another variation of the invention where upper or post-operative interface socket 310 with upper back shell 311 is used with lower socket 611. In this variation both upper rear or back shell 311 of interface socket 310 and upper shell 615 of lower socket 611 help immobilize the knee of the amputee during the initial healing process. Thus once the healing process is complete both shell 311 and 615 can be removed to allow the amputee to flex his or her knee.

IV An Alternative Single Socket Post-Operative Perpetual Dimension Prosthetic System In another embodiment of the invention the prosthetic system consists of a single socket. In this embodiment it has a front shell 801 FIG. 18. Front shell 801 has an extended surface 801A that is shaped to fit against the front of a trans-tibial amputee's leg or limb. Extended surface 801A of the front shell terminates in a base 801B that will be below the bottom of the amputee's limb, Dome 831 provides room to accommodate the amputee's knee. As will be discussed below, since front shell 801 will be the main weight bearing part of the single socket system it must be made of a semi rigid load bearing material. In the preferred embodiment polypropylene is used to make front shell 801. Polypropylene is easy to work with and form into the desired shape and is strong enough to bear the full Load of an amputee's body when walking or running.

Figures 18, 19:
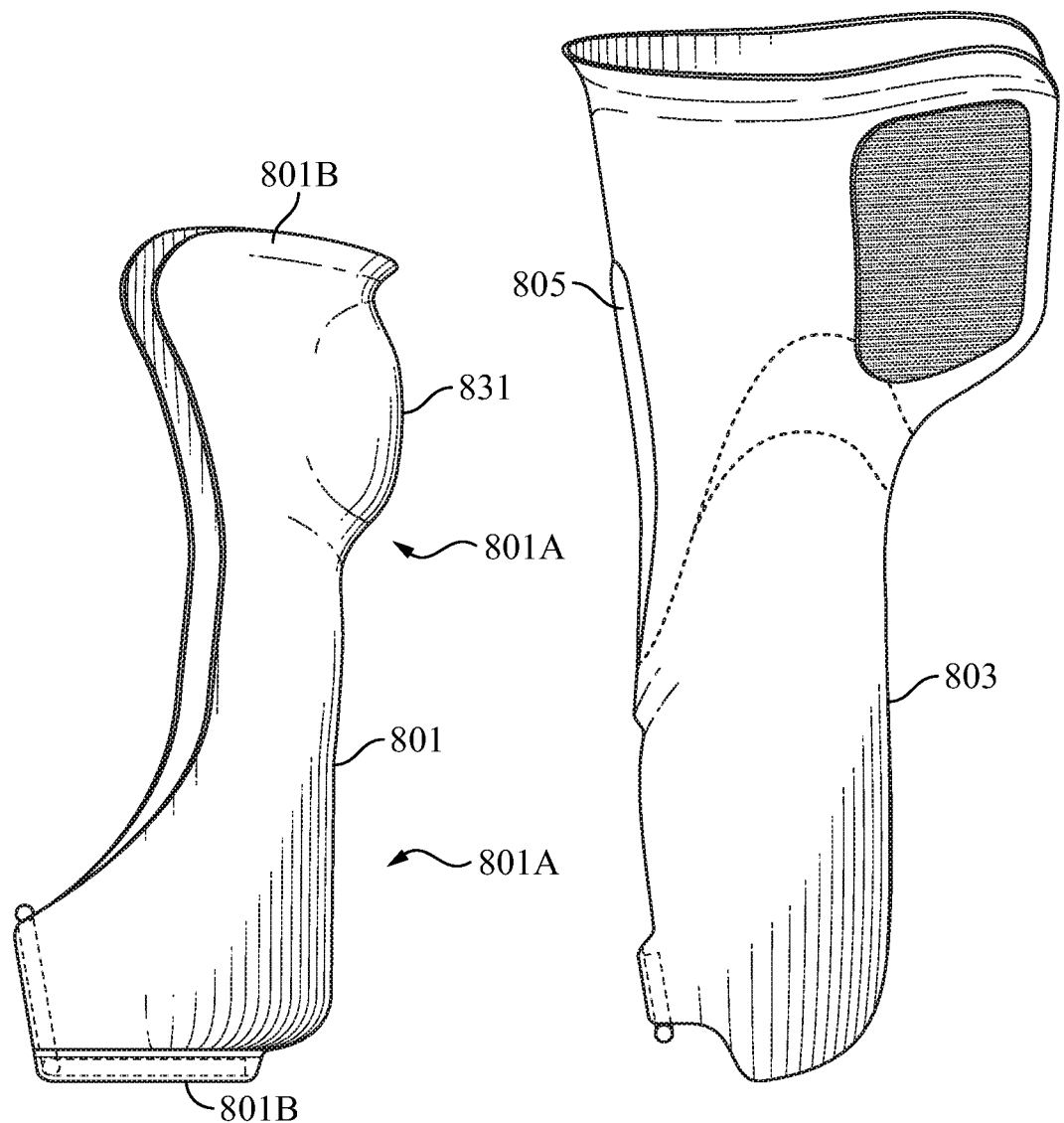
FIG. 18 is a side view of a front shell of an embodiment of the invention that has a single socket.
FIG. 19 is a side view of the rear shell of the variation of the invention that has a single socket.

FIG. 19 is a side view of an embodiment of the rear shell 803 of the single socket prosthesis of the present invention. As can be seen rear shell 803 has an extended surface configured to fit against the rear of the leg of an amputee. Rear shell 803 is made of a pliable and formable material. In the preferred embodiment it is made of polyethylene.

The front shell and rear shell are attached by articulated hinge 711 FIGS. 16A and 16B. Referring now to FIG. 20 which provides a side view of the single socket embodiment 800 of the invention fully assembled. It includes front shell 801 connected to the rear shell 803 by hinge 711 shown in outline since it is inside the shells. Plate 711A attaches to a top inside surface of base 8018B and plate 711C attaches to a bottom edge of rear shell 803. Center plate 711B of articulated hinge 711 only connects at pivot points with plates 711A and 711C and thus can move when plates 711A or 711C move.

Foot 445 is connected by shaft 441 to hardware 443 and reinforced bottom connection plate 442 of front shell 801. Reinforced connection plate 442 is a reinforced portion of front shell 801 capable of carrying the load put on it by the amputee when waling or standing.

FIG. 21 shows how the space between the front shell 801 and the rear shell 803 can be varied by articulated hinge 711. As noted above since plate 711B of hinge 711 is only hingedly connected to plates 711A and 711C it can move to allow shell move with respect to shell 801 and change the space between the two shells. As noted previously after an amputation of a limb, the remaining portion of the amputated limb varies in size over the course of the amputee's recovery from the surgery. Initially it will swell as a result of the trauma of the surgery. Subsequently it will also shrink as the patient recovers. It will shrink as a result of the need to minimize use of the limb during recovery. In Particular with a post-operative transitional amputation this includes immobilizing the knee of the amputee until the surgical wound created by the surgery has fully healed.

Figure 22:
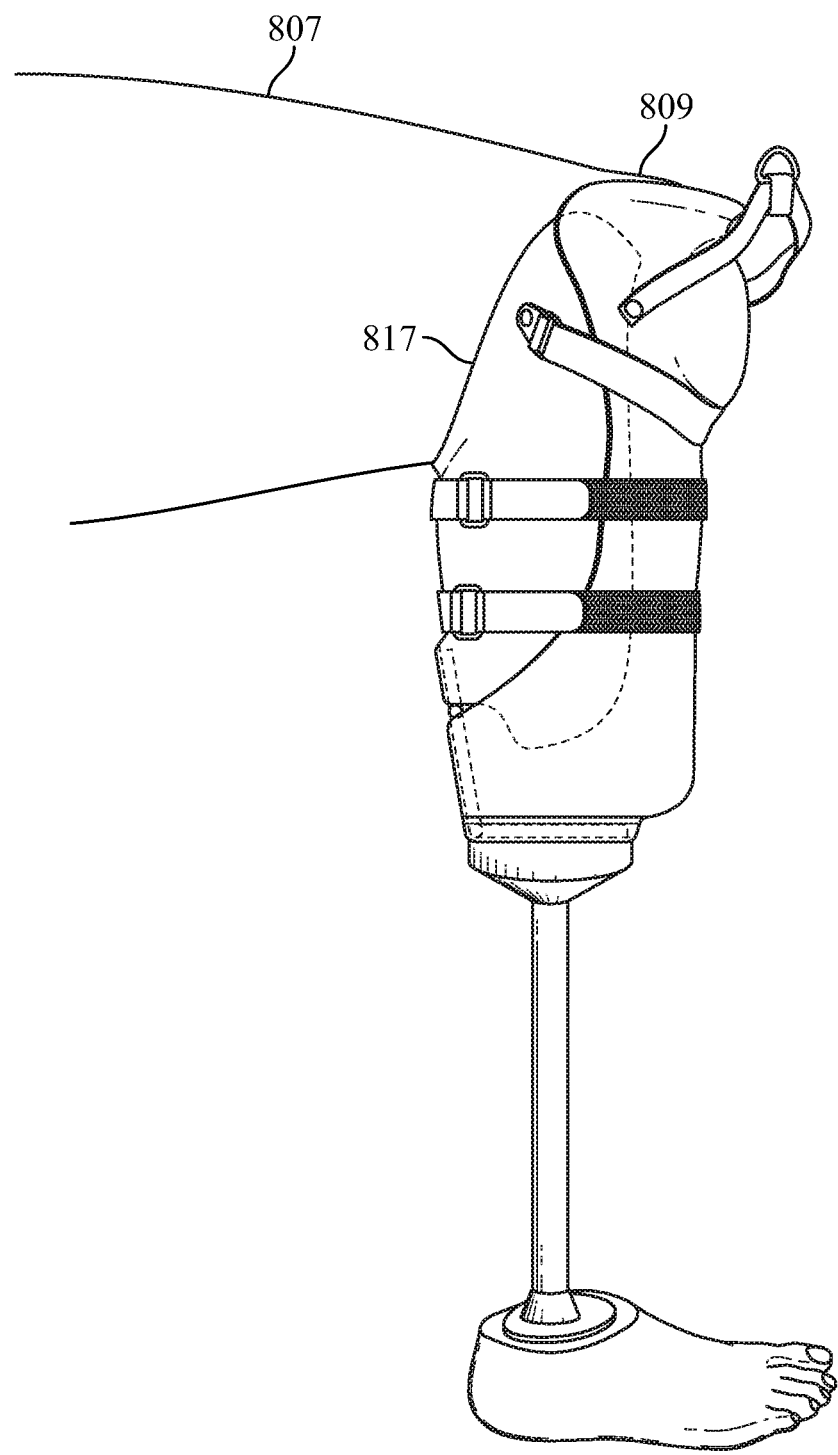
FIG. 22 depicts the single socket prosthetic system with the upper portion of the rear shell removed along a trim line after post-operative recovery to allow the amputee to flex his or her leg.
Figure 23:
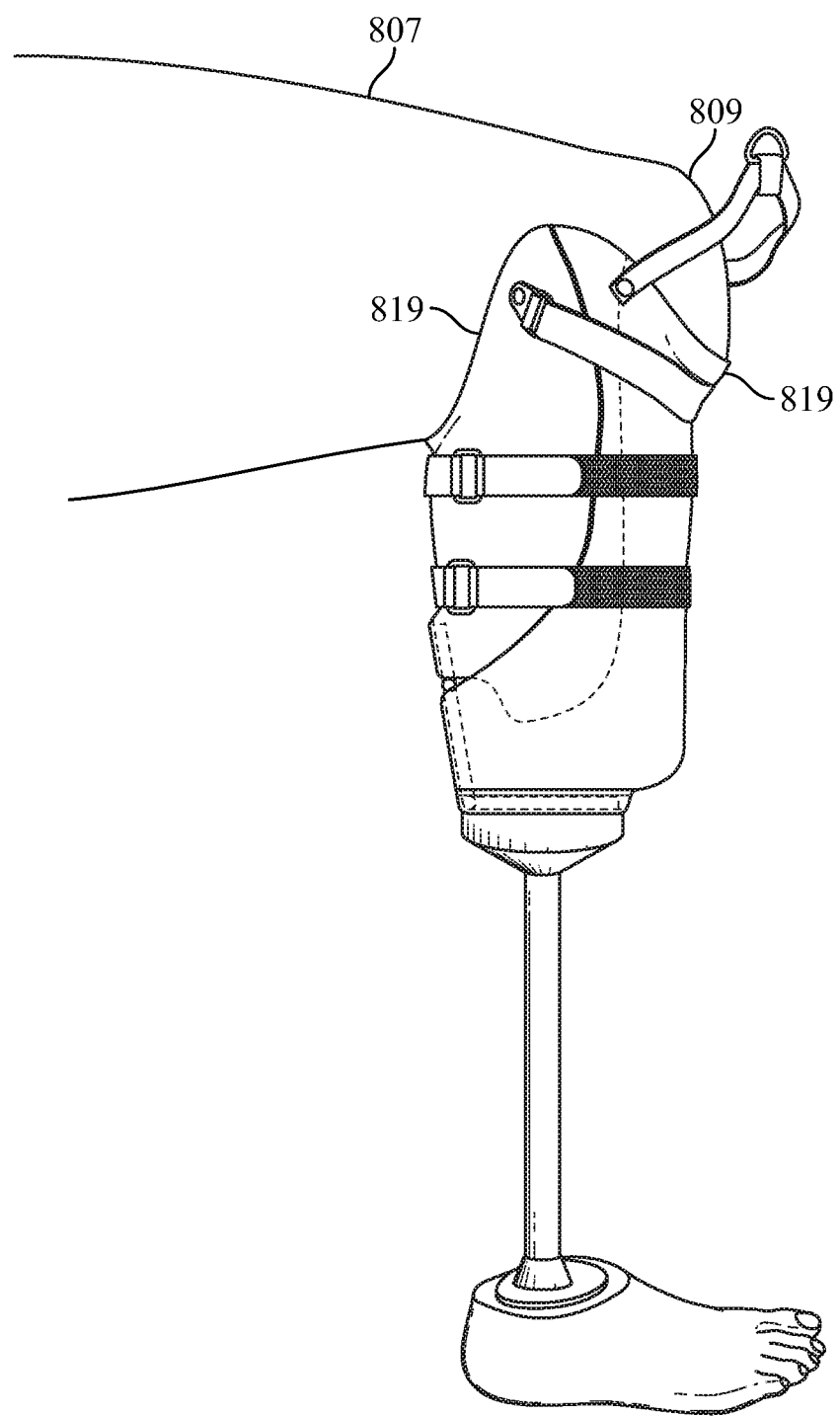
FIG. 23 depicts the single socket prosthetic system with the upper portion of the rear shell and front shell removed along another trim line after post-operative recovery to allow the amputee to flex his or her leg.

Referring to FIGS. 22 and 23 once the amputee has recovered from the operation and can begin exercising his or her leg the upper portion 805 of the rear shell 803 can be removed to allow the amputee to flex his or her leg 807 and bend the knee and begin therapy to walk in a normal fashion. Additionally, parts of upper portions 801C of the front shell can also be removed. As previously discussed above with respect to the two socket version of the invention the shells can be cut along different trim lines three of which are: 1) Supra Condylar Supra Patellar (SCSP) trim line, 2) super condylar (SC) trim line and 3) Patellar tendon bearing (PTB) trim line (FIGS. 6A, 6B and 6C). Referring back to FIG. 22 it provides an example of a SCSP trim line cut 817 of the single socket system. Likewise FIG. 23 is an example of PTB trim line cut 819. Naturally, the trim line cut can be varied significantly to achieve optimal movement and support which can include a super condylar (SC) as depicted in FIG. 6B. Thus, any number of variations of cuts can be made depending on the needs of the particular amputee. As depicted in FIGS. 22 and 23 once the trim line cut is made it allows the amputee to move his limb 807 and flex his or her knee 809.

V. An Apparatus for Dimensional Changes of the Socket

In another aspect of the invention it includes an apparatus for positioning and fixing the dimensional changes of the space between the front and back shells of the sockets that are connected by an articulated hinge. Referring to FIG. 21 as depicted therein two spacing and positioning wedges 821A and 821B are positioned between center plate 711 of articulated hinged 711 and the back rim 801D of base 801B of front shell 801.

Figure 24:
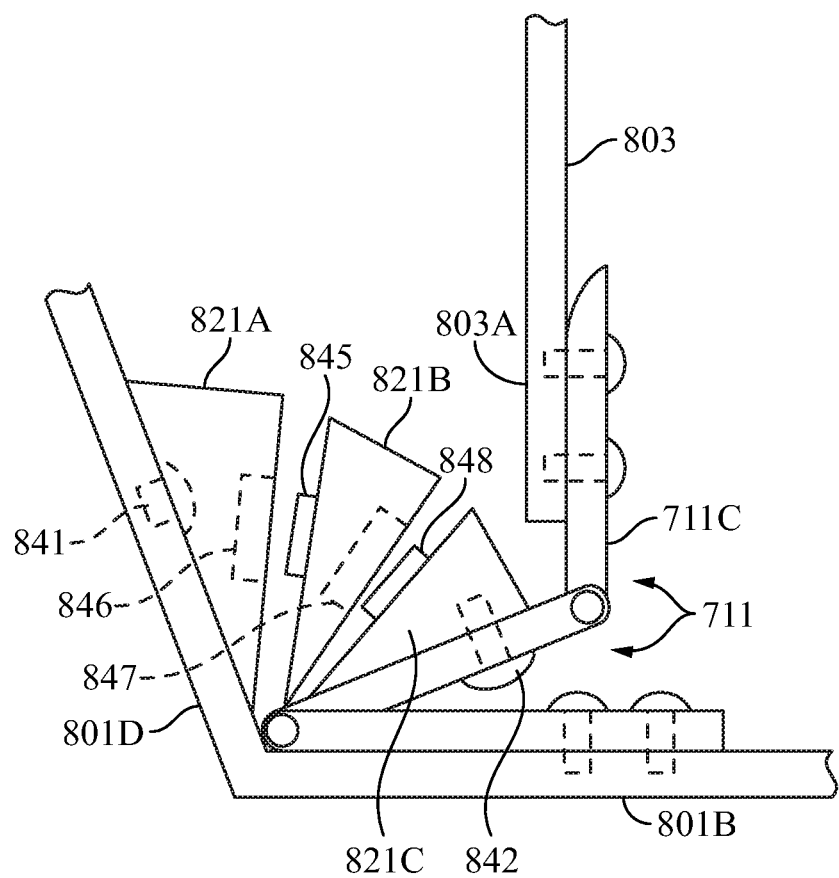
FIG. 24 is a schematic diagram one variation of a system that uses wedges to position and secure the position of the front shell and rear shell when they are connected by an articulated hinge.

By varying the number of wedges from none to 3, the position of center plate 711B can be fixed. FIG. 24 provides a schematic of the wedge positioning system of the present invention. Articulated hinge 711 connects by plate 711C to a lower portion 803A of rear shell 803. Plate 711A of hinge 711 connects to the inside of bottom base 801B of the front shell Rear rim 801. Spacing wedges 821A, 821B, and 821C are depicted in a semi-exploded view are positioned between rear rim 801D of base 801B of front shell 801 and center hinge plate 711B. In the embodiment depicted in FIG. 24, wedge 821A connects to rear rim 801D by retaining screw 841. Wedge 821C connects to center hinge plate 711B by retaining screw 843. Wedge 821B has knob 845 which fits into recess 846. Wedge 821C has knob 847 which fits into recess 848 of wedge. Thus, when wedges 821A, 821B, and 821C are inserted and connected together they are held in place.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An interface socket for a trans-tibial amputee comprising:
    a. a base cup;
    b. a lower back shell attached to said base cup by a flexible back strut having a first end and a second end;
        i. said first end being connected to said lower back shell at a point above a bottom edge of said lower back shell with a first set of open ended slots on either side of said flexible back strut, said first set of open ended slots open at said bottom edge of said lower back shell and terminate at opposite closed ends where said first end of said flexible back strut connects to said lower back shell;
        ii. said second end being connected to a bottom of said base cup with a second set of open ended slots on either side of said flexible back strut, said second set of open ended slots open at a rim of said base cup and terminate at a closed end adjacent to said connection of said second end to said bottom of said base cup; and
        iii. said back strut having a bend in it that positions a plane formed by said base of said base cup approximately perpendicular to a plane formed by a line up a middle of said lower back shell;
    c. an upper back shell connected to a top edge of said lower back shell;
    d. a front shell connected to said base cup by a flexible front strut;
    e. wherein said interface socket is made of a flexible, resilient and formable material;
    f. wherein said lower back shell is movable in relation to said front shell to vary said space between said lower back shell and said front shell; and
    g. wherein said front shell and said lower back shell with said upper back shell attached are positioned to form a space therebetween to receive a limb of a trans-tibial amputee and be adjusted to vary the space therebetween to hold and grip said limb in a secure and comfortable fashion.

2. The interface socket of claim 1 wherein said upper back shell is detachably connected to said top edge of said lower back shell and thus said upper back shell can be removed to allow said amputee to flex a knee of the amputated limb.

3. The interface socket of claim 2 wherein said detachable connection is selected from a group consisting of a) a super condylar super patellar trim line, b) a supra condylar trim line, and c) patellar tendon bearing trim line.

4. The interface socket of claim 1 wherein:
    a. said flexible front strut has a first end connected to a portion of said rim of said base cup opposite a bottom edge of said front shell;
    b. said flexible front strut has a second end connected to a portion of a bottom of said front shell with open ended slots on either side of said flexible front strut forming said bottom edge of said front shell separated from and opposite from a portion of said rim of said base cup on either side of said flexible front strut; and
    c. wherein said structure described allows for a flexing of side edges of said front shell to thereby allow said side edges of said front shell to slip inside of outside of edges of said lower back shell when said front shell and said back shell are moved towards each other to decrease the space therebetween.

5. The interface socket of claim 1 wherein said opposite closed ends of said first set of open end slots terminate at a circular aperture adjacent to the first end of said back strut; and said second set of open ended slots on either side of said flexible front strut terminate at a closed end with a circular aperture.

6. The interface socket of claim 4 wherein said open ended slots terminate at closed end circular apertures.

7. The interface socket of claim 1 wherein said flexible, resilient and formable material is polyethylene.

8. A lower socket for holding and supporting an interface socket comprising:
    a. a bottom cup;
    b. a front shell connected to a front top edge of said bottom cup;
    c. a back shell attached to said bottom cup by an articulated adjustable strut;
    d. wherein said lower socket is made of a flexible, resilient and formable material; and
    e. wherein said articulated adjustable strut comprises a center plate with a first plate hingedly attached at a first edge of said center plate and a second plate attached at a second edge or said center opposite said first edge, wherein said first plate is detachably connected to said back shell and said second plate is detachably connected to said bottom cup; and f. wherein said front shell and said back shell form an interior space to accept an interface socket and said space between said front shell and said back shell can be varied by movement of said articulated strut to accommodate post-operative interface sockets of varying sizes.

9. The lower socket of claim 8 wherein said flexible, resilient and formable material is polypropylene.

10. The lower socket of claim 8 wherein an upper shell detachably connects to said back shell, wherein when said upper shell is removed an amputee wearing said lower socket can flex the knee of an amputated limb wearing said lower shell.

11. A prosthetic system for amputees that have undergone a trans-tibial amputation comprising:

a, a post-operative interface socket comprising:
 i. a base cup;
 ii. a lower back shell attached to said base cup by a flexible back strut having a first end and a second end,
  said first end being connected to said lower back shell at a point above a bottom edge of said lower back shell with a first set of open ended slots on either side of said flexible back strut, said first set of open ended slots open at said bottom edge of said lower back shell and terminate at their opposite end where said first end of said flexible back strut connects to said lower back shell;
  said second end being connected to a bottom of said base cup with a second set of open ended slots on either side of said flexible back strut, said second set of open ended slots open at a rim of said base cup and terminate at a closed end adjacent to said connection of said second end to said bottom of said base cup; and
  said back strut has a bend in it that positions a plane formed by said base of said base cup approximately perpendicular to a plane of formed by a line up a middle of said lower back shell;
 iii. an upper back shell connected to a top edge of said lower back shell;
 iv. a front shell connected to said base cup by a flexible front strut, said flexible front strut having a first end and a second end, said first end connected to a portion of said rim of said base cup opposite a bottom edge of said front shell, and said second end connected to a portion of a bottom of said front shell with open ended slots on either side of said flexible front strut forming said bottom edge of said front shell separated from and opposite from a portion of said rim of said base cup;
 v. wherein said interface socket is made of a flexible, resilient and formable material; and
 vi. wherein said lower back shell is movable in relation to said front shell to vary said space between said lower back shell and said front shell;
 vii. wherein said structure described allows for a flexing of side edges of said front shell to thereby allow said side edges of said front shell to slip inside of outside of edges of said lower back shell; and
 viii. wherein said front shell and said back shell are positioned to form a space there between to receive a limb of a trans-tibial amputee and be adjusted to vary the space there between to hold and grip said limb in a secure and comfortable fashion;

b. A lower socket for holding and supporting said post-operative interface socket comprising:
 i. a bottom cup:
 ii. a front shell connected to a top edge of a front of said bottom cup;
 iii. a back shell attached to said bottom cup by an articulated adjustable strut;
 iv. wherein said lower socket is made of a flexible, resilient and formable material; and
 v. wherein said front shell and said back shell form an interior space to accept a post-operative interface socket and said space between said front shell and said back shell can be varied by movement of said articulated strut to accommodate post-operative interface sockets of varying sizes.

12. The prosthetic system of claim 11 wherein said post-operative interface socket is made from polyethylene and said lower socket is made from polypropylene.

13. The prosthetic system of claim 11 wherein said upper back shell of said post-operative interface socket is detachably connected to said top edge of said lower back shell and thus said upper back shell can be removed to allow said amputee to flex a knee of the amputated limb.

14. The prosthetic system of claim 11 wherein an upper shell detachably connects to said back shell of said lower socket, wherein when said upper shell is removed an amputee wearing said lower socket can flex the knee of an amputated limb wearing said lower shell.

15. The prosthetic system of claim 11 wherein said upper back shell is detachably connected to said top edge of said lower back shell and wherein an upper shell detachably connects to said back shell wherein when said upper shell and said upper back shell are removed an amputee wearing said prosthetic system can flex the knee of an amputated limb wearing said prosthetic system.

16. The prosthetic system of claim 13 wherein said detachable connection is selected from a group consisting of a) a super condylar super patellar trim line, b) a supra condylar trim line, and c) patellar tendon bearing trim line.

17. A single socket adjustable prosthetic system comprising:

a. a first shell with an extended surface configured to fit against a first side of an amputee's limb, said surface terminating at a base, said base configured to extend under the amputee's limb and said base having a limb facing surface and a bottom surface;
b. a second shell with an extended surface configured to fit against a second side of the amputee's limb;
c. an articulated hinge having three plates, a center plate with a first plate hingedly attached at a first end of said center plate and a second plate hingedly attached at a second end of said center plate, with said first plate of said articulated hinge attached to said base and said second plate of said articulated hinge attached to said second shell; and
d. said articulated hinge connected at said first plate to said base of said first shell and connected at said second plate to said second shell forms a space between said first shell and said second shell, said space to be varied to hold, and accommodate swelling and shrinking of the amputee's limb.

18. The single socket adjustable prosthetic system of claim 17 wherein:

a. a shaft connects at a top end to the bottom surface of said base and projects downwards from said base to a bottom end;
b. a prosthetic foot attaches to said bottom end of said shaft; and
c. wherein when said system is attached to a remaining portion of a limb of the amputee, said amputee can use said limb to stand and for mobility.

19. The single socket adjustable prosthetic system of claim 17 wherein:
a. said first shell is made of a semi rigid load bearing material; and
b. said second shell is made of a pliable and formable material.

20. The single socket adjustable prosthetic system of claim 19 wherein said semi rigid load bearing material said first shell is made of is polypropylene and said pliable and formable material said second shell is made from is polyethylene.

21. The single socket adjustable prosthetic system of claim 17 wherein:
a. the amputee has had a trans-tibial amputation and the first side of the amputee's limb is the front of the limb and the second side of the amputee's limb is the rear of the limb;
b. said second shell has an upper portion such that when said single socket adjustable prosthetic system is attached to the amputee's limb the amputee is prevented from bending of the knee;
c. said first shell has an upper portion that covers and protects the knee of the amputee; and
d. a trim line can be cut that removes portions of the upper portion of the second shell and can remove portions of said upper portion of said first shell, to thereby allow the amputee to flex the knee when said single socket is attached to the amputee's leg.

22. The single socket adjustable prosthetic system of claim 21 wherein the trim line cut of said upper portion of said second shell and said first shell is selected from the group consisting of: a supra condylar supra patellar (SCSP) trim line, a supra condylar (SC) trim line, and a patellar tendon bearing (PTB) trim line.

23. The single socket adjustable prosthetic system of claim 17 further comprising a hinge positioning and securing system wherein:
a. said base of said first shell has a rim around a rear portion of said base opposite the connection of said extended surfaces connection to said base;
b. said hinged attachment of said first plate to said center plate is positioned at the base of said rim when said first plate is connected to said interior of said base; and
c. said center plate can be positioned at different positions from said rim by insertion of at least one wedge between said center plate and said rim.

24. The single socket adjustable prosthetic system of claim 17 wherein said first plate of said articulated hinge is attached to the limb facing surface of said base and said second plate of said articulated hinge is attached to a limb facing surface of said second shell.

* * * * *